United States Patent
Sadis et al.

(10) Patent No.: US 10,421,994 B2
(45) Date of Patent: Sep. 24, 2019

(54) PROGNOSTIC ASSAY FOR SQUAMOUS CELL LUNG CARCINOMA

(71) Applicant: LIFE TECHNOLOGIES CORPORATION, Carlsbad, CA (US)

(72) Inventors: Seth Sadis, Ann Arbor, MI (US); Paul Williams, Ann Arbor, MI (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 15/948,908

(22) Filed: Apr. 9, 2018

(65) Prior Publication Data

US 2018/0298423 A1 Oct. 18, 2018

Related U.S. Application Data

(63) Continuation of application No. 14/210,124, filed on Mar. 13, 2014.

(60) Provisional application No. 61/798,889, filed on Mar. 15, 2013.

(51) Int. Cl.
*C12Q 1/6886* (2018.01)
*C12Q 1/686* (2018.01)

(52) U.S. Cl.
CPC ........... *C12Q 1/686* (2013.01); *C12Q 1/6886* (2013.01); *C12Q 2600/118* (2013.01); *C12Q 2600/156* (2013.01)

(58) Field of Classification Search
CPC ................. C12Q 1/6886; C12Q 2600/156
See application file for complete search history.

(56) References Cited

PUBLICATIONS

Pantel, K. et al. Journal of the National Cancer Institute 91(13):1113 (1999).*
Akervall, J et al., "The Gene Ratios cMYC:Cyclin-dependent Kinase (CDK)N2A and CCND1:CDKN2A Correlate with Poor Prognosis in Squarnous Cell Carcinoma of the Head and Neck", *Clinical Cancer Research*, 1750 vol. 9., May 2003, 1750-1755.
Hammerman, P et al., "Suppl. 2", *Journal of Thoracic Oncology*, vol. 6, No. 6, Jun. 2011, S39.
Hammerman, P et al., "Supplementary Data", *Nature*, 7.1, Sep. 2012, 489-519.
Hammerman, P. et al., "Comprehensive genomic characterization of squamous cell lung cancers", *Nature*, vol. 489, Sep. 27, 2012, 519-525.
Hammerman, P. et al., "P16 Supplementary Data—Comprehensive genomic characterization of squamous cell lung cancers (Data File S7.1)", *NIH Publications*, Retrieved from the internet: URL: https: //tcga-data.nci.nih.gov/docs/publications/lusc_2012/LUSC_p16_Suppl_Table.html, Sep. 27, 2012, 5 pgs.
Hammerman, P. et al., "Supplementary Information—Comprehensive genomic characterization of squamous cell lung cancers", *Nature*, Retrieved from the Internet: URL: http://www.nature.com/nature/journal/v489/n7417/extref/nature11404-s1.pdf, Sep. 27, 2012, 1-75.

(Continued)

*Primary Examiner* — Diana B Johannsen

(57) ABSTRACT

Methods for predicting clinical outcome for a human subject diagnosed with squamous cell lung carcinoma using a panel of molecular markers that includes CDKN2A and CCND1. The markers are related to the subject's increased likelihood of a negative clinical outcome.

20 Claims, 14 Drawing Sheets

(56) References Cited

PUBLICATIONS

Jin, M. et al., "Cyclin D1, p16 and retinoblastoma gene product expression as a predictor for prognosis in non-small cell lung cancer at stages I and II", *Lung Cancer*, vol. 34, Nov. 1, 2001, 207-218.

Mizuaral, S et al., "Expression ratio of CCND1 to CDKN2A mRNA predicts RB1 status of cultured cancer cell lines and clinical tumor samples", *Molecular Cancer*, vol. 10 (31), 2011, 1-11.

Myong, N , "Cyclin D1 Overexpression, p16 Loss, and pRb Inactivation Play a Key Role in Pulmonary Carcinogenesis and have a Prognostic Implication for the Long-term Survival in Non-small Cell Lung Carcinoma Patients", *Cancer research and Treatment*, 40(2), 2008, 45-52.

Namazie, A. et al., "Cyclin D1 Amplification and p16 (MTS1/CDK4I) Deletion Correlate With Poor Prognosis in Head and Neck Tumors", *The Laryngoscope*, vol. 112, Mar. 2002, 472-481.

PCT/US2014/026724, , "International Search Report and Written Opinion dated Jul. 11, 2014", Jul. 11, 2014, 14 Pages.

Smeds, J. et al., "Genetic status of cell cycle regulators in squamous cell carcinoma of the oesophagus: the CDKN2A (p16INK4a and p14ARF) and p53 genes are major targets for inactivation", *Carcinogenesis*, vol. 23, No. 4, Jan. 14, 2002, 645-655.

\* cited by examiner

CDKN2A mutation
p 0.051

CDND1 amp
p 0.076

CDKN2A DEL
p 0.18

PROGNOSTIC ASSAY FOR SQUAMOUS CELL LUNG CARCINOMA

CROSS-REFERENCE TO RELATED APPLICATIONS

This application is a Continuation of U.S. patent application Ser. No. 14/210,124 filed on Mar. 13, 2014, which claims priority to U.S. Patent Application No. 61/798,889 filed Mar. 15, 2013, each of which are herein incorporated by reference in their entirety.

FIELD

The present invention relates to squamous cell lung carcinoma and multigene assays for predicting survival rate of patients with this cancer.

BACKGROUND

Patients with early stage lung cancer are typically treated with surgery followed by watchful waiting. A large fraction of these patients experience recurrence within 5 years. A prognostic assay is not yet available for squamous cell lung carcinoma, the second major histological subtype of non-small cell lung cancer. Accordingly, there is a need for a prognostic assay for squamous cell lung carcinoma.

SUMMARY

In one aspect, the present invention provides a method of predicting clinical outcome for a human subject diagnosed with squamous cell lung carcinoma comprising: (a) determining the presence of a loss of function mutation in the cyclin-dependent kinase inhibitor 2A (CDKN2A) or deletion of the gene in a biological sample comprising cancer cells obtained from said human subject; (b) determining the presence of an increase in the copy number of the G1/S-specific cyclin-D1 (CCND1) gene in a biological sample comprising cancer cells obtained from said human subject; and (c) predicting the clinical outcome for said human subject, wherein the presence of a loss of function mutation in the CDKN2A gene or deletion of the gene and increase in the copy number of the CCND1 gene positively correlates with an increased likelihood of a negative clinical outcome, and wherein the absence of a loss of function mutation in the CDKN2A gene or deletion of the gene or absence of an increase in the copy number of the CCND1 gene positively correlates with an increased likelihood of a positive clinical outcome.

In some embodiments, the loss of function mutation in the CDKN2A gene is a missense mutation, nonsense mutation, or frameshift mutation, or any combination thereof. In some of these, the missense mutation is a D108G, D108N, D108Y, G125R, P114L mutation, or any combination thereof.

In some embodiments, the increase in copy number of the CCND1 gene is greater than or equal to 4.

In some embodiments, the determining the presence of a loss of function mutation in the CDKN2A gene comprises contacting the biological sample with reagents to: (a) amplify the gene or a portion thereof comprising said mutation to provide an amplification product of the gene or portion thereof, or (b) reverse transcribe a RNA transcript encoded by the CDKN2A gene comprising said mutation and amplify the reverse transcription product to provide an amplification product of the gene or portion thereof.

In some of these, the presence of said mutation in the amplification product is determined by next generation sequencing.

In some of these, the presence of said mutation in the amplification product is determined by qPCR.

In some of these, the reagents are oligonucleotides.

In some of these, the reagents are PCR primer sets. In others, the reagents are RT-PCR primer sets.

In some embodiments, the squamous cell lung carcinoma is stage I.

In some embodiments, the squamous cell lung carcinoma is stage II.

In some embodiments, the biological sample is obtained from a surgically resected tumor.

In some embodiments, the predicting of clinical outcome provides a 5-year mortality risk assessment.

In another aspect, the present invention provides a kit comprising reagents to amplify the CDKN2A gene comprising a loss of function mutation, or portion of the gene comprising the loss of function mutation.

In some embodiments, the reagents are PCR primer sets.

In another aspect, the present invention provides a kit comprising reagents to reverse transcribe a RNA transcript encoded by the CDKN2A gene comprising a loss of function mutation.

In some embodiments, the reagents are RT-PCR sets.

In another aspect, the present invention provides a method of determining a treatment plan for a human subject having squamous cell lung cancer, the method comprising: (a) determining the presence of a loss of function mutation in the cyclin-dependent kinase inhibitor 2A (CDKN2A) gene or deletion of the gene in a biological sample comprising cancer cells obtained from said human subject; (b) determining the presence of an increase in the copy number of the G1/S-specific cyclin-D1 (CCND1) gene in a biological sample comprising cancer cells obtained from said human subject; (c) predicting the clinical outcome for said human subject, wherein the presence of a loss of function mutation in the CDKN2A gene or deletion of the gene and increase in the copy number of the CCND1 gene positively correlates with an increased likelihood of a negative clinical outcome, and wherein the absence of a loss of function mutation in the CDKN2A gene or deletion of the gene or absence of an increase in the copy number of the CCND1 gene positively correlates with an increased likelihood of a positive clinical outcome; (d) determining a risk assessment for 5-year mortality based on the prediction; and (e) devising a treatment plan based on the risk assessment.

In another aspect, the present invention provides a system for determining a treatment for a patient diagnosed with squamous cell lung carcinoma comprising: (a) a processor; (b) a patient database that receives patient data from a treating provider, wherein the patient data includes:
   i) identification of a loss of function mutation in the cyclin-dependent kinase inhibitor 2A (CDKN2A) gene or deletion of the gene in a biological sample comprising cancer cells obtained from said patient;
   ii) identification of an increase in the copy number of the G1/S-specific cyclin-D1 (CCND1) gene in a biological sample comprising cancer cells obtained from said patient;
   iii) a correlation of the presence of a loss of function mutation in the CDKN2A gene or deletion of the gene with an increase in the copy number of the CCND1 gene, wherein the correlation is indicative of increased likelihood of a negative clinical outcome; and (c) a treatment protocol database that is populated with one or more treatment protocols that provide guidelines for treating patients with the correlation of b), iii); and (d) determining a treatment protocol.

In another aspect, the present invention provides a method of identifying a human subject diagnosed with squamous cell lung carcinoma as a candidate for post-surgical adjuvant therapy, the method comprising: (a) determining the presence of a loss of function mutation in the cyclin-dependent kinase inhibitor 2A (CDKN2A) gene or deletion of the gene in a biological sample comprising cancer cells obtained from said human subject; and (b) determining the presence of an increase in the copy number of the G1/S-specific cyclin-D1 (CCND1) gene in a biological sample comprising cancer cells obtained from said human subject; wherein the presence of a loss of function mutation in the CDKN2A gene or deletion of the gene and increase in the copy number of the CCND1 gene positively correlates with an increased likelihood of a negative clinical outcome and identifies the human subject as a candidate for post-surgical adjuvant therapy.

In some embodiments, the post-surgical adjuvant therapy is chemotherapy, radiation therapy, or a combination thereof.

In another aspect, the present invention provides a method of treating squamous cell lung carcinoma in a patient comprising; (a) obtaining a biological sample from the patient containing squamous cell lung carcinoma cells obtained from surgical resection of the cancer; (b) determining the presence of a loss of function mutation in the cyclin-dependent kinase inhibitor 2A (CDKN2A) gene or deletion of the gene in the biological sample; (c) determining the presence of an increase in the copy number of the G1/S-specific cyclin-D1 (CCND1) gene in the biological sample; (d) identifying a patient having squamous cell lung carcinoma cells comprising a loss of function mutation in the CDKN2A gene or deletion of the gene and increase in the copy number of the CCND1 gene; and (e) treating the patient with post-surgical adjuvant therapy.

In some embodiments, the post-surgical adjuvant therapy is chemotherapy, radiation therapy, or a combination thereof.

DETAILED DESCRIPTION

Figure 1:
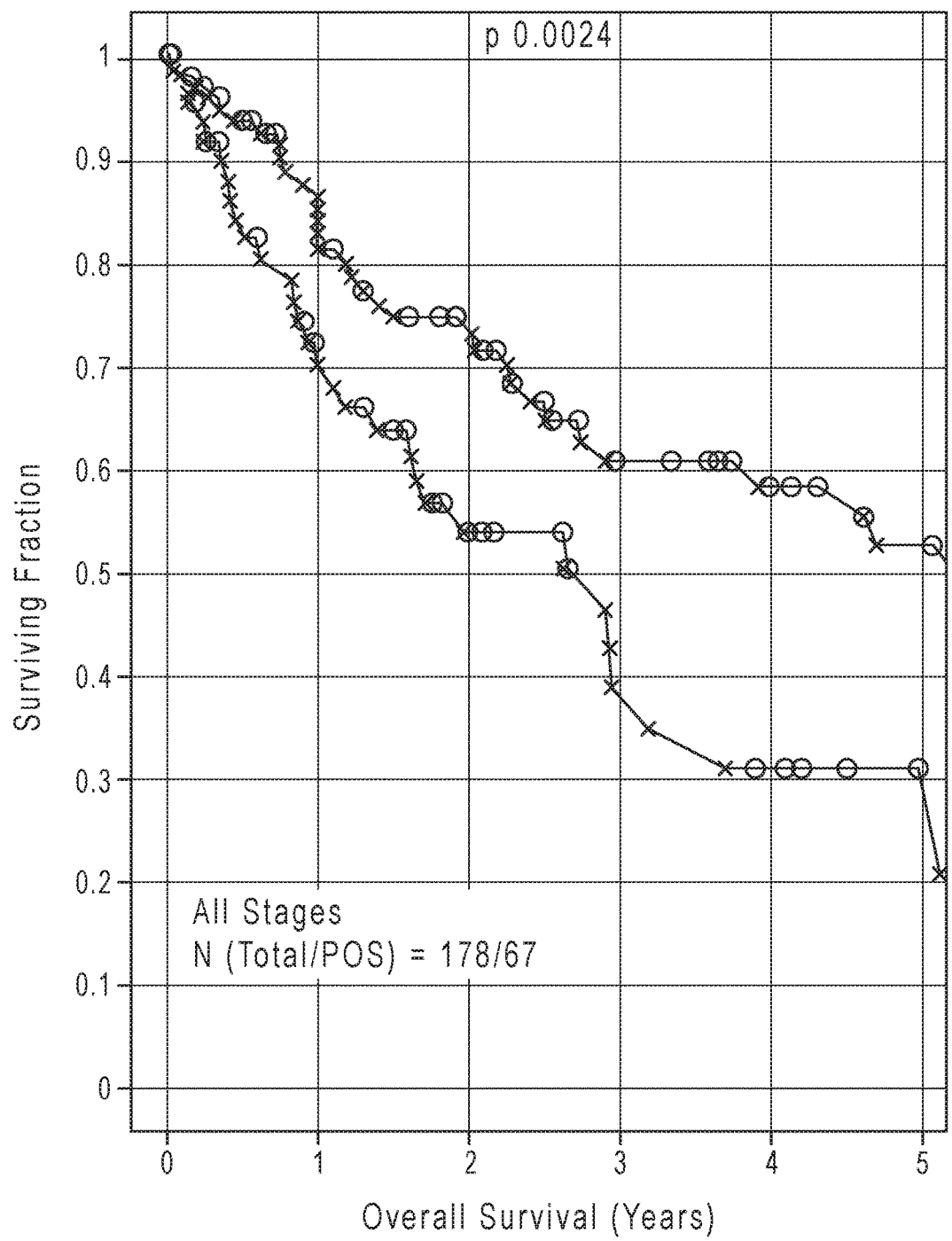
FIG. 1 shows the analysis of mixed-stage patient population of 175 patients with squamous cell lung carcinoma. In this figure and the following figures, the upper curve shows the events associated with each patient who did not have an aberration of the G1/S pathway, while the lower curves shows the events associated with each patient who had an aberration of the G1/S pathway. In each curve, "x" indicates death, while "o" represents survival at last follow-up.

The novel features of the invention are set forth with particularity in the appended claims. A better understanding of the features and advantages of the present invention will be obtained by reference to the following detailed description that sets forth illustrative embodiments and accompanying drawing, in which the principles of the invention are utilized.

Definitions

"Lung cancer" refers generally to two main types of lung cancer categorized by the size and appearance of the malignant cells: non-small cell (approximately 80% of cases) and small-cell (roughly 20% of cases) lung cancer. "Non-small cell lung cancer" (NSCLC) includes squamous cell carcinoma. Lung adenocarcinoma is the most common subtype of NSCLC, and other subtypes of lung cancer include bronchioloalveolar carcinoma, large cell carcinoma, carcinoid, adenoid cystic carcinoma, cylindroma, and mucoepidermoid carcinoma. In one embodiment, lung cancers are staged according to stages I-IV, with I being an early stage and IV being the most advanced.

"Prognosis" refers, e.g., to overall survival, long term mortality, and disease free survival. In one embodiment, long term mortality refers to death within 5 years after diagnosis of lung cancer.

"Risk assessment" refers to the relative risk an individual faces with respect to mortality. For example, a prognosis providing a high risk assessment for 5-year mortality has a greater likelihood of mortality within 5 years than an individual having a low risk assessment for 5-year mortality. In one embodiment, the prognosis for long term mortality is "high risk," e.g., high risk of mortality, "intermediate risk," e.g., intermediate risk of mortality, or "low risk," e.g., low risk of mortality. The stage of cancer and the prognosis may be used to tailor a patient's therapy to provide a better outcome, e.g., systemic therapy and surgery, surgery alone, or systemic therapy alone. Risk assessment can be divided as desired, e.g., at the median, in tertiary groups, quaternary groups, and so on.

The term "marker" refers to a molecule (typically protein, nucleic acid, carbohydrate, or lipid) that is expressed in the cell, expressed on the surface of a cancer cell or secreted by a cancer cell in comparison to a non-cancer cell, and which is useful for the diagnosis of cancer, for providing a prognosis, and for preferential targeting of a pharmacological agent to the cancer cell. Oftentimes, such markers are molecules that are overexpressed in a lung cancer or other cancer cell in comparison to a non-cancer cell, for instance, 1-fold overexpression, 2-fold overexpression, 3-fold overexpression or more in comparison to a normal cell. Further, a marker can be a molecule that is inappropriately synthesized in the cancer cell, for instance, a molecule that contains deletions, additions or mutations in comparison to the molecule expressed on a normal cell. Alternatively, such biomarkers are molecules that are underexpressed in a cancer cell in comparison to a non-cancer cell, for instance, 1-fold underexpression, 2-fold underexpression, 3-fold underexpression, or more. Further, a marker can be a molecule that is inappropriately synthesized in cancer, for instance, a molecule that contains deletions, additions or mutations in comparison to the molecule expressed on a normal cell.

It will be understood by the skilled artisan that markers may be used in combination with other markers or tests for any of the uses, e.g., prediction, diagnosis, or prognosis of cancer, disclosed herein.

"Biological sample" includes sections of tissues such as biopsy and autopsy samples, and frozen sections taken for histologic purposes. Such samples include blood and blood fractions or products (e.g., serum, platelets, red blood cells, and the like), sputum, bronchoalveolar lavage, cultured cells, e.g., primary cultures, explants, and transformed cells, stool, urine, etc. A biological sample is typically obtained from a eukaryotic organism, most preferably a mammal such as a primate e.g., chimpanzee or human; cow; dog; cat; a rodent, e.g., guinea pig, rat, mouse; rabbit; or a bird; reptile; or fish.

A "biopsy" refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the tissue type to be evaluated (e.g., lung etc.), the size and type of the tumor, among other factors. Representative biopsy techniques include, but are not limited to, excisional biopsy, incisional biopsy, needle biopsy, surgical biopsy, and bone marrow biopsy. An "excisional biopsy" refers to the removal of an entire tumor mass with a small margin of normal tissue surrounding it. An "incisional biopsy" refers to the removal of a wedge of tissue from within the tumor. A diagnosis or prognosis made by endoscopy or radiographic guidance can require a "core-needle biopsy", or a "fine-needle aspiration biopsy" which generally obtains a suspension of cells from within a target tissue. Biopsy techniques are discussed, for example, in *Harrison's Principles of Internal Medicine*, Kasper, et al., eds., 16th ed., 2005, Chapter 70, and throughout Part V.

The terms "overexpress," "overexpression," or "overexpressed" interchangeably refer to a protein or nucleic acid (RNA) that is translated or transcribed at a detectably greater level, usually in a cancer cell, in comparison to a normal cell. The term includes overexpression due to transcription, post transcriptional processing, translation, post-translational processing, cellular localization (e.g., organelle, cytoplasm, nucleus, cell surface), and RNA and protein stability, as compared to a normal cell. The term also includes overexpression due to chromosomal copy number increase. Overexpression can be detected using conventional techniques for detecting copy number increase (PCR, fluorescent in situ hybridization, comparative genomic hybridization and with high-resolution array-based tests based on array comparative genomic hybridization (or aCGH) and SNP array technologies), mRNA (i.e., RT-PCR, PCR, hybridization) or proteins (i.e., ELISA, immunohistochemical techniques). Overexpression can be 10%, 20%, 30%, 40%, 50%, 60%, 70%, 80%, 90% or more in comparison to a normal cell. In certain instances, overexpression is 1-fold, 2-fold, 3-fold, 4-fold or more higher levels of transcription or translation in comparison to a normal cell.

The terms "underexpress," "underexpression," or "underexpressed" or "downregulated" interchangeably refer to a protein or nucleic acid that is translated or transcribed at a detectably lower level in a cancer cell, in comparison to a normal cell. The term includes underexpression due to gene deletion, mutation of a gene rendering the gene non-functional with respect to transcription or translation, transcription, post transcriptional processing, translation, post-translational processing, cellular localization (e.g., organelle, cytoplasm, nucleus, cell surface), and RNA and protein stability, as compared to a control. Underexpression can be detected using conventional techniques for detecting mRNA (i.e., RT-PCR, PCR, hybridization) or proteins (i.e., ELISA, immunohistochemical techniques). Underexpression can be 0%, 10%, 20%, 30%, 40%, 50%, 60%, 70%, 80%, 90% or less in comparison to a control. In certain instances, underexpression is 1-fold, 2-fold, 3-fold, 4-fold or more lower levels of transcription or translation in comparison to a control.

The term "differentially expressed" or "differentially regulated" refers generally to a protein or nucleic acid that is overexpressed (upregulated) or underexpressed (downregulated) in one sample compared to at least one other sample, generally in a cancer patient compared to a sample of non-cancerous tissue in the context of the present invention.

The term, "therapeutic treatment" and "cancer therapies" refers to chemotherapy, hormonal therapy, radiotherapy, immunotherapy, and biologic (targeted) therapy.

By "therapeutically effective amount or dose" or "sufficient amount or dose" herein is meant a dose that produces effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-0-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., 11161. *Cell. Probes* 8:91-98 (1994)). The term nucleic acid is used interchangeably with gene, cDNA, mRNA, oligonucleotide, and polynucleotide.

A particular nucleic acid sequence also implicitly encompasses "splice variants" and nucleic acid sequences encoding truncated forms of a protein. Similarly, a particular protein encoded by a nucleic acid implicitly encompasses any protein encoded by a splice variant or truncated form of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. Nucleic acids can be truncated at the 5' end or at the 3' end. Polypeptides can be truncated at the N-terminal end or the C-terminal end. Truncated versions of nucleic acid or polypeptide sequences can be naturally occurring or recombinantly created.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M). See, e.g., Creighton, *Proteins* (1984).

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al., supra.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding. Antibodies can be polyclonal or monoclonal, derived from serum, a hybridoma or recombinantly cloned, and can also be chimeric, primatized, or humanized.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain ($V_l$) and variable heavy chain (Va) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce $F(ab')_2$, a dimer of Fab which itself is a light chain joined to $V_H$-$C_H1$ by a disulfide bond. The $F(ab')_2$ may be reduced under mild conditions to break the disulfide linkage in the hinge region, thereby converting the F(ab)'2 dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

In one embodiment, the antibody is conjugated to an "effector" moiety. The effector moiety can be any number of molecules, including labeling moieties such as radioactive labels or fluorescent labels, or can be a therapeutic moiety. In one aspect the antibody modulates the activity of the protein.

The nucleic acids of the differentially expressed genes of this invention or their encoded polypeptides refer to all forms of nucleic acids (e.g., gene, pre-mRNA, mRNA) or proteins, their polymorphic variants, alleles, mutants, and interspecies homologs that (as applicable to nucleic acid or protein): (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 25, 50, 100, 200, 500, 1000, or more amino acids, to a polypeptide encoded by a referenced nucleic acid or an amino acid sequence described herein; (2) specifically bind to antibodies, e.g., polyclonal antibodies, raised against an immunogen comprising a referenced amino acid sequence, immunogenic fragments thereof, and conservatively modified variants thereof; (3) specifically hybridize under stringent hybridization conditions to a nucleic acid encoding a referenced amino acid sequence, and conservatively modified variants thereof; (4) have a nucleic acid sequence that has greater than about 95%, preferably greater than about 96%, 97%, 98%, 99%, or higher nucleotide sequence identity, preferably over a region of at least about 25, 50, 100, 200, 500, 1000, or more nucleotides, to a reference nucleic acid sequence. A polynucleotide or polypeptide sequence is typically from a mammal including, but not limited to, primate, e.g., human; rodent, e.g., rat, mouse, hamster; cow, pig, horse, sheep, or any mammal. The nucleic acids and proteins of the invention include both naturally occurring or recombinant molecules. Truncated and alternatively spliced forms of these antigens are included in the definition.

The phrase "specifically (or selectively) binds" when referring to a protein, nucleic acid, antibody, or small molecule compound refers to a binding reaction that is determinative of the presence of the protein or nucleic acid, such as the differentially expressed genes of the present invention, often in a heterogeneous population of proteins or nucleic acids and other biologics. In the case of antibodies, under designated immunoassay conditions, a specified antibody may bind to a particular protein at least two times the background and more typically more than 10 to 100 times background. Specific binding to an antibody under such conditions requires an antibody that is selected for its specificity for a particular protein. For example, polyclonal antibodies can be selected to obtain only those polyclonal antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity).

The phrase "functional effects" in the context of assays for testing compounds that modulate a marker protein includes the determination of a parameter that is indirectly or directly under the influence of a biomarker of the invention, e.g., a chemical or phenotypic. A functional effect therefore includes ligand binding activity, transcriptional activation or repression, the ability of cells to proliferate, the ability to migrate, among others. "Functional effects" include in vitro, in vivo, and ex vivo activities.

By "determining the functional effect" is meant assaying for a compound that increases or decreases a parameter that is indirectly or directly under the influence of a biomarker of the invention, e.g., measuring physical and chemical or phenotypic effects. Such functional effects can be measured by any means known to those skilled in the art, e.g., changes in spectroscopic characteristics (e.g., fluorescence, absorbance, refractive index); hydrodynamic (e.g., shape), chromatographic; or solubility properties for the protein; ligand binding assays, e.g., binding to antibodies; measuring inducible markers or transcriptional activation of the marker; measuring changes in enzymatic activity; the ability to increase or decrease cellular proliferation, apoptosis, cell cycle arrest, measuring changes in cell surface markers. The functional effects can be evaluated by many means known to those skilled in the art, e.g., microscopy for quantitative or qualitative measures of alterations in morphological features, measurement of changes in RNA or protein levels for other genes expressed in placental tissue, measurement of RNA stability, identification of downstream or reporter gene expression (CAT, luciferase, β-gal, GFP and the like), e.g., via chemiluminescence, fluorescence, colorimetric reactions, antibody binding, inducible markers, etc.

"Inhibitors," "activators," and "modulators" of the markers are used to refer to activating, inhibitory, or modulating molecules identified using in vitro and in vivo assays of cancer biomarkers. Inhibitors are compounds that, e.g., bind to, partially or totally block activity, decrease, prevent, delay activation, inactivate, desensitize, or down regulate the activity or expression of cancer biomarkers. "Activators" are compounds that increase, open, activate, facilitate, enhance activation, sensitize, agonize, or up regulate activity of cancer biomarkers, e.g., agonists. Inhibitors, activators, or modulators also include genetically modified versions of cancer biomarkers, e.g., versions with altered activity, as well as naturally occurring and synthetic ligands, antagonists, agonists, antibodies, peptides, cyclic peptides, nucleic acids, antisense molecules, ribozymes, RNAi and siRNA molecules, small organic molecules and the like. Such assays for inhibitors and activators include, e.g., expressing cancer biomarkers in vitro, in cells, or cell extracts, applying putative modulator compounds, and then determining the functional effects on activity, as described above.

Samples or assays comprising cancer biomarkers that are treated with a potential activator, inhibitor, or modulator are compared to control samples without the inhibitor, activator, or modulator to examine the extent of inhibition. Control samples (untreated with inhibitors) are assigned a relative protein activity value of 100%. Inhibition of cancer biomarkers is achieved when the activity value relative to the control is about 80%, preferably 50%, more preferably 25-0%. Activation of cancer biomarkers is achieved when the activity value relative to the control (untreated with activators) is 110%, more preferably 150%, more preferably 200-500% (i.e., two to five fold higher relative to the control), more preferably 1000-3000% higher.

The term "test compound" or "drug candidate" or "modulator" or grammatical equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, peptide, circular peptide, lipid, fatty acid, siRNA, polynucleotide, oligonucleotide, etc., to be tested for the capacity to directly or indirectly modulate cancer biomarkers. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 daltons and less than about 2500 daltons, preferably less than about 2000 daltons, preferably between about 100 to about 1000 daltons, more preferably between about 200 to about 500 daltons.

Methods of Predicting Clinical Outcome

In one aspect, the present invention provides methods of predicting clinical outcome for a human subject diagnosed with squamous cell lung carcinoma comprising: (a) determining the presence of a loss of function mutation in the cyclin-dependent kinase inhibitor 2A (CDKN2A) or deletion of the gene in a biological sample comprising cancer cells obtained from said human subject; (b) determining the presence of an increase in the copy number of the G1/S-specific cyclin-D1 (CCND1) gene in a biological sample comprising cancer cells obtained from said human subject; and (c) predicting the clinical outcome for said human subject, wherein the presence of a loss of function mutation in the CDKN2A gene or deletion of the gene and increase in the copy number of the CCND1 gene positively correlates with an increased likelihood of a negative clinical outcome, and wherein the absence of a loss of function mutation in the CDKN2A gene or deletion of the gene or absence of an increase in the copy number of the CCND1 gene positively correlates with an increased likelihood of a positive clinical outcome.

The predicting clinical outcome for a human subject diagnosed with squamous cell lung carcinoma involves determining the level of a panel of lung cancer biomarker polynucleotide or the corresponding polypeptides in the subject or subject sample and then comparing the level to a baseline or range. Typically, the baseline value is representative of levels of the polynucleotide or nucleic acid in a healthy person not suffering from, or destined to develop, lung cancer, as measured using a biological sample such as a lung biopsy or a sample of a bodily fluid. Variation of levels of a polynucleotide or corresponding polypeptides of the invention from the baseline range (either up or down) indicates that the patient has an increased risk of long term mortality.

In some embodiments, it is determined whether the CDKN2A gene in the biological sample from the subject is deleted or mutated such that it is rendered non-functional e.g., being non-functional in the G1/S cell cycle pathway of the squamous cell lung cancer cell. In some embodiments, the mutations may be a loss of function mutation, such as, for example, a missense mutation, nonsense mutation, or frameshift mutation, or any combination thereof. In some of these embodiments, the missense mutation may be a D108G, D108N, D108Y, G125R, P114L mutation, or any combination thereof.

In some embodiments, it is determined whether there is an increase in the copy number of the CCND1 in biological sample from the subject. In some of these embodiments, the increase in copy number of this gene may be about 4 and in other embodiments the increase in copy number may be more than 4, such as, for example, 5, 6, 7, 8, 9, 10, etc.

In some embodiments, it is determined whether the CDKN2A gene is deleted or mutated such that it is rendered non-functional in a lung cancer cell of the subject, and whether there is an increase in the copy number of the CCND1 in the biological sample.

In some embodiments, the presence of a loss of function mutation in the CDKN2A gene or deletion of the gene may be detected by PCR or RT-PCR, followed by Next Generation Sequencing (NGS) or q-PCR. Using PCR, the CDKN2A gene or a portion thereof comprising the mutation in the biological sample may be amplified to produce an amplification product of the gene or portion thereof. Using RT-PCR, the RNA transcript encoded by the CDKN2A gene comprising the mutation can be reverse transcribed to cDNA comprising the mutation, which in turn can amplified to provide an amplification product of the gene or portion thereof.

The amplification product of the CDKN2A gene or portion thereof comprising the loss of function mutation can be confirmed by sequencing using NGS methods or by qPCR.

NGS methods, which are high throughput sequencing methods, are well known those skilled in the art. Such methods include single-molecule real-time sequencing (Pacific Bio), Ion semiconductor sequencing (Life Technologies), Pyrosequencing (454), Sequencing by synthesis (Ion Torrent Sequencing, Illumina), and Sequencing by ligation (SOLiD sequencing, Life Technologies). To perform these types of sequencing, commercial sequencers are available, for example, Life Technologies' SOLiD™ sequencer, Roche's 454™ sequencer, Illumina's HiSeg™ sequencer, LifeTechnologies' Ion Torrent™ sequencer, and Illumina's MiSeg™ sequencer.

qPCR is well known to those skilled in the art. qPCR is a laboratory technique based on the PCR, which may be used to amplify and simultaneously quantify a targeted DNA molecule. For one or more specific sequences in a DNA sample, qPCR enables both detection and quantification. The quantity can be either an absolute number of copies or a relative amount when normalized to DNA input or additional normalizing genes. The data generated can be analyzed by computer software to calculate relative gene expression (or mRNA copy number) in several samples. qPCR may also be applied to the detection and quantification of DNA in samples to determine the presence and abundance of a particular DNA sequence in these samples, such as, for example the loss of function mutations in the CDKN2A gene as described above.

In some embodiments, the copy number of the CCND1 gene in the biological sample from the subject may be determined by methods well known to those skilled in the art. Examples of copy number variation determinations include fluorescent in situ hybridization, comparative genomic hybridization and with high-resolution array-based tests based on array comparative genomic hybridization (or aCGH) and SNP array technologies as described, for example, in Langer-Safer P R et al. (July 1982), *Proc. Natl. Acad. Sci. U.S.A.* 79 (14): 4381-5; Sher G et al., (January 2009), *Fertil. Steril.* 92 (6): 1886-1894; Ren H et al. (May 2005), *Human Mutation* 25 (5): 476-82; and McCarroll S A et al. (2008), *Nature Genetics,* 40: 1166-1174.

In some embodiments, the determination of the presence of a loss of function mutation in the CDKN2A gene or deletion of the gene in a biological sample comprising cancer cells obtained from the human subject or the presence of an increase in the copy number of the CCND1 gene in the biological sample, or both, may be performed by determining the differential expression of the one or both of these genes.

Various technological approaches for determination of expression levels of the panel of genes are set forth herein, including, but not limited to, RT-PCR, microarrays, high-throughput sequencing, serial analysis of gene expression (SAGE) and Digital Gene Expression (DGE). The expression level of each gene may be determined in relation to various features of the expression products of the gene including exons, introns, protein epitopes and protein activity.

In some embodiments, real time or quantitative reverse transcription PCR (RT-PCR) is used to examine expression of the CDKN2A gene and CCND1 gene in a biological sample comprising cancer cells obtained from said human subject using RNA from the biological sample. No microdissection is required. RNA extraction can be performed by any method known to those of skill in the art, e.g., methods involving proteinase K tissue digestion and alcohol-based nucleic acid precipitation, treatment with DNAse to digest contaminating DNA, RNA purification using silica-gel-membrane technology, methods utilizing commercially available kits such as Trizol and RNeasy, or any combination thereof. Real time RT-PCR can be performed by any method known to those of skill in the art, e.g., Taqman real time PCR using Applied Biosystem assays. Gene expression is calculated relative to pooled normal lung RNA, and expression is normalized to housekeeping genes. Suitable oligonucleotide primers are selected by those of skill in the art.

In one embodiment, RNA biomarkers are examined using nucleic acid binding molecules such as probes, oligonucleotides, oligonucleotide arrays, and primers to detect differential RNA expression in a biological sample comprising cancer cells obtained from said human subject. In one embodiment, RT-PCR is used according to standard methods known in the art. In another embodiment, quantitative RT-PCR assays such as those utilizing Taqman® assays available from, e.g., Applied Biosystems, can be used to detect nucleic acids and variants thereof. In other embodiments, nucleic acid microarrays can be used to detect nucleic acids. Analysis of nucleic acids can be achieved using routine techniques such as Northern analysis, or any other methods based on hybridization to a nucleic acid sequence that is complementary to a portion of the marker coding sequence (e.g., slot blot hybridization) are also within the scope of the present invention. Reagents that bind to selected nucleic acid biomarkers can be prepared according to methods known to those of skill in the art or purchased commercially.

The risk assessment of a human subject diagnosed with squamous cell cancer may be based on the predicting the clinical outcome for the subject by categorizing the subject's risk based on the properties of the CDKN2A gene, CCND1 gene, or CDKN2A and CCND1 genes found in a biological sample comprising cancer cells obtained from the subject and how they are associated with a high risk or low risk of mortality.

In some embodiments, the risk assessment may be performed using the determination of the presence of a loss of function mutation in the CDKN2A gene or deletion of the gene in the biological sample.

In some embodiments, the risk assessment may be performed using the determination of the presence of an increase in the copy number of the CCND1 gene in the biological sample.

In some embodiments, the risk assessment may be performed using the determination of the presence of a loss of function mutation in the CDKN2A gene or deletion of the gene in the biological sample and the determination of the presence of an increase in the copy number of the CCND1 gene in the biological sample.

In some embodiments, the presence of a loss of function mutation in the CDKN2A gene or deletion of the gene and increase in the copy number of the CCND1 gene positively correlates with an increased likelihood of a negative clinical outcome.

In some embodiments, the absence of a loss of function mutation in the CDKN2A gene or deletion of the gene or absence of an increase in the copy number of the CDKN2A gene positively correlates with an increased likelihood of a positive clinical outcome.

Based on the determination of risk, subjects may be partitioned into risk groups, e.g., high risk or low risk. Risk groups can further be classified on different ranges of mortality, for example, on 6 month, 1-year, 2-year, 3-year, 4-year, 5-year, 10-year, 25-year mortality.

In some embodiments, based on the determination of risk, a risk groups may be classified for a 5-year mortality.

Risk groups can further be classified on different ranges of events associated with squamous cell lung cancer, which can include, but is not limited to, likelihood of metastasis, recurrence, etc.

In certain embodiments, the method comprises performing the actionable treatment recommendation. Accordingly, performing the actionable treatment recommendation can include, without limitation, administering a therapeutically effective amount of one or more therapeutic agents (chemotherapeutics, targeted therapeutics, antiangiogenics, etc), implementing a dietary regimen, administering radiation and/or enrolling in one or more clinical trials.

Examples of chemotherapeutics to treat lung cancer include: Cisplatin or carboplatin, gemcitabine, paclitaxel, docetaxel, etoposide, and/or vinorelbine. Targeted therapeutics (drugs that specifically block the growth and spread of cancer) include monoclonal antibodies such as, but not limited to, bevacizumab (AVASTIN™) and cetuximab; and tyrosine kinase inhibitors (TKIs) such as, but not limited to, gefitinib (IRESSA™), erlotinib (TARCEVA™) crizotinib and/or vemurafenib.

Additional chemotherapeutics to treat lung cancer include, but are not limited to, TKIs: vandetanib, tofacitinib, sunitinib malate, sorafenib, ruxolitinib, regorafenib, ponatinib, pazopanib, nilotinib, leflunomide, lapatinib ditosylate, imatinib mesilate, gefitinib, erlotinib, dasatinib, crizotinib, cabozantinib, bosutinib, axitinib, radotinib, tivozanib, masitinib, afatinib, XL-647, trebananib, tivantinib, SAR-302503, rilotumumab, ramucirumab, plitidepsin, pacritinib, orantinib, nintedanib, neratinib, nelipepimut-S, motesanib diphosphate, midostaurin, linifanib, lenvatinib, ibrutinib, fostamatinib disodium, elpamotide, dovitinib lactate, dacomitinib, cediranib, baricitinib, apatinib, Angiozyme, X-82, WBI-1001, VX-509, varlitinib, TSR-011, tovetumab, telatinib, RG-7853, RAF-265, R-343, R-333, quizartinib dihydrochloride, PR-610, poziotinib, PLX-3397, PF-04554878, Pablocan, NS-018, momelotinib, MK-1775, milciclib maleate, MGCD-265, linsitinib, LDK-378, KX2-391, KD-020, JNJ-40346527, JI-101, INCB-028060, icrucumab, golvatinib, GLPG-0634, gandotinib, foretinib, famitinib, ENMD-2076, danusertib, CT-327, crenolanib, BMS-911543, BMS-777607, BMS-754807, BMS-690514, bafetinib, AZD-8931, AZD-4547, AVX-901, AVL-301, AT-9283, ASP-015K, AP-26113, AL-39324, AKN-028, AE-37, AC-480, 2586184, X-396, volitinib, VM-206, U3-1565, theliatinib, TAS-115, sulfatinib, SB-1317, SAR-125844, S-49076, rebastinib, R84 antibody, Peregrine, R-548, R-348, PRT-062607, P-2745, ONO-4059, NRC-AN-019, LY-2801653, KB-004, JTE-052, JTE-051, IMC-3C5, ilorasertib, IDN-6439, HM-71224, HM-61713, henatinib, GSK-2256098, epitinib, EMD-1214063, E-3810, EOS, CUDC-101, CT-1578, cipatinib, CDX-301, CC-292, BI-853520, BGJ-398, ASP-3026, ARRY-614, ARRY-382, AMG-780, AMG-337, AMG-208, AL-3818, AC-430, 4SC-203, Z-650, X-379, WEE-1/CSN5, Tekmira Pharmaceuticals, Wee-1 kinase inhibitors, Tekmira Pharmaceuticals, VS-4718, VEGFR2 inhibitor, AB Science, VEGF/rGel, Clayton Biotechnologies, VEGF inhibitors, Interprotein, UR-67767, tyrosine kinase inhibitors, Bristol-Myers Squibb, tyrosine kinase inhibitor, Aurigene Discovery Technologies, tyrosine kinase 2 inhibitors, Sareum, TrkA ZFP TF, TrkA inhibitor, Proximagen, TP-0903, TP-0413, TKI, Allergan, Sym-013, syk kinase inhibitors, Almirall, Syk kinase inhibitors, AbbVie, SYK inhibitor programme, Ziarco, SUN-K706, SN-34003, SN-29966, SIM-930, SIM-6802, SIM-010603, SGI-7079, SEL-24-1, SCIB-2, SAR-397769, RET kinase inhibitor, Bionomics, R-256, PRT-062070, PRT-060318, PRS-110, PLX-7486, ORS-1006, ORB-0006, ORB-0004, ORB-0003, ONO-WG-307, ON-044580, NVP-BSK805, NNI-351, NMS-P948, NMS-E628, NMS-173, MT-062, MRLB-11055, MG-516, KX2-361, KIT816 inhibitor, AB Science, janus kinase inhibitor, Celgene, JAK3-inhibitor, Principia BioPharma, Jak1 inhibitor, Genentech, JAK inhibitors, Almirall, INCB-16562, hR1-derivatives, Immunomedics, HMPL-281, HM-018, GTX-186, GSK-143, GS-9973, GFB-204, gastrointestinal stromal tumour therapy, Clovis Oncology, G-801, FX-007, FLT4 kinase inhibitors, Sareum, FLT3/cKit inhibitor, Johnson & Johnson, flt-4 kinase inhibitors, Sareum, flt-3 kinase inhibitors, Sareum, FAK inhibitors, Takeda, FAK inhibitor, Verastem, EN-3351, DNX-04040, DNX-02079, DLX-521, deuterated tofacitinib, Auspex Pharmaceuticals, DCC-2721, DCC-2701, DCC-2618, CTX-0294945, CTx-0294886, CT-340, CT-053, CST-102, CS-510, CPL-407-22, CH-5451098, CG-206481, CG-026828, CFAK-C4, CCT-137690, CC-509, c-Met kinase inhibitors, Rhizen, BXL-1H5, BTK inhibitors, Mannkind, Btk inhibitor, Pharmacyclics-3, Btk inhibitor, Aurigene Discovery Technologies, BGB-324, BGB-001, Bcr-Abl/Lyn inhibitor, AB Science, aurora kinase+FLT3 kinase inhibitor, Sareum, aurora kinase+ALK inhibitor, Sareum, aurora kinase+ALK inhibitor, AstraZeneca, ASP-502D, ASP-08112, ARYY-111, AR-523, anticancer, leukaemia, Critical, anticancer therapy, Agios-1, ANG-3070, ALK inhibitors, AstraZeneca, Alk inhibitor, Cephalon-3, ALK inhibitor, Aurigene Discovery Technologies, AL-2846, TrkB modulators, Hermo Pharma, TLK-60596, TLK-60404, CYC-116, ARRY-380, ZD-4190, Yissum Project No. B-1146, XL-999, XL-820, XL-228, VX-667, vatalanib, tyrosine protein kinase inhibs, tyrosine kinase inhibs, Yissum, tyrosine kinase inhibs, CSL, tyrosine kinase antags, ICRT, tozasertib lactate, TG-100-13, tandutinib, TAK-593, TAK-285, Symadex, Syk kinase inhibitor, SGX, SU-5271, SU-14813, SGX-523, semaxanib, saracatinib, RP 53801, RG-14620, RG-13291, RG-13022, R-112, PLX-647, PKI-166, Pharmaprojects No. 6085, Pharmaprojects No. 4960, Pharmaprojects No. 4923, Pharmaprojects No. 4863, Pharmaprojects No. 3624, Pharmaprojects No. 3292, Pharmaprojects No. 3054, PF-562271, PF-4217903, NVP-TAE226, mubritinib, MEDI-547, lestaurtinib, KW-2449, KSB-102, KRN-633, IMC-EB10, GW-282974, Flt3-kinase inhibitor, Lilly, FCE-26806, EphA2 vaccine, MedImmune, EMD-55900, EMD-1204831, desmal, degrasyns, CNF-201 series, CGP-57148, CEP-7055, CEP-5214, CEP-075, CE-245677, CDP-860, canertinib dihydrochloride, cancer vaccine, Ajinomoto, bscEphA2xCD3, MedImmune, brivanib alaninate, breast cancer therapy, Galapago, BIBX-1382, AZD-9935, AZD-6918, AZD-4769, AZD-1480, AVE-0950, Argos, AP-23464, AP-23451, AP-22408, anti-HER2/neu mimetic, Cyclacel, anti-HER-2/neu antisense, Tekm, amuvatinib, AG-490, AG-18, AG-13958, AEG-41174, ZM-254530, ZK-CDK, ZK-261991, ZD-1838, ZAP70 kinase inhibitors, Kinex, ZAP-70 inhibitors, Cellzome, ZAP inhibitors, Ariad, ZAP 70 inhibitors, Galapagos, ZAP 70 inhibitors, Celgene, YW327.6S2, YM-359445, YM-231146, YM-193306, XV-615, XL-019, XC-441, XB-387, Wee-1 kinase inhibitor, Banyu, VX-322, VRT-124894, VEGFR2 kinase inhibitors, Takeda, VEGFR/EGFR inhib, Amphora, VEGFR-2 kinase inhibitors, Hanmi, VEGFR-2 antagonist, Affymax, VEGF/rGel, Targa, VEGF-TK inhibitors, AstraZeneca, VEGF-R inhibitors, Novartis, VEGF modulators, 3-D, VEGF inhibitors, Onconova, VEGF inhibitor, Chugai, V-930, U3-1800, U3-1784, tyrphostins, Yissum, tyrosine kinase inhibs, Novar-2, tyrosine kinase inhibs, Sanofi, tyrosine kinase inhib, Abbott-2, tyrosine kinase inhib, Pfizer, tyrosine kinase inhib, IQB, tyrosine kinase inhib, Abbott, tyrosine kinase inhi, Abbott-3, trkB inhibitors, Amphora, TrkA inhibitors, Telik, TrkA blocker, Pfizer, TLN-232, TKM-0150, Tie-2 kinase inhibitors, GSK, TIE-2 inhibitors, Ontogen, Tie-2 inhibitors, AstraZeneca, Tie-2 inhibitors, Amgen-3, Tie-2 inhibitors, Amgen-2, Tie-2 inhibitors, Amgen, Tie-2 antagonists, Semaia, Tie-1R IFP, Receptor BioLogix, TG-101-223, TG-101-209, TG-100948, TG-100435, TG-100-96, TG-100-801, TG-100-598, TAE-684, T3-106, T-cell kinase inhibitors, Cell, syk kinase inhibitor, Bayer, Syk inhibitors, CrystalGenomics, Syk inhibitors, Astellas-2, Syk inhibitors, Amphora, SU-11657, SU-0879, SSR-106462, SRN-004, Src/Abl inhibitors, Ariad, Src non-RTK antagonists, SUGEN, Src inhibitors, Amphora, spiroindolines, Pfizer, SP-5.2, sorafenib bead, Biocompatibles, SMi-11958, SH2 inhibitors, NIH, SH-268, SGX-393, SGX-126, SGI-1252, SC-102380, SC-101080, SB-238039, SAR-131675, RWJ-64777, RWJ-540973, RPR-127963E, RP-1776, Ro-4383596, RNAi cancer therapy, Benitec Biopharma, RM-6427, rheumatoid arthritis therapy, SRI International, RET inhibitors, Cell T, RB-200h, R545, Rigel, R3Mab, R-723, R-507, R-499, R-1530, QPMS-986, QPAB-1556, PX-104.1, PS-608504, prostate cancer ther, Sequenom, prodigiosin, PRI-105, PP1, Scripps, PN-355, phenylalanine derivatives, NIH, Pharmaprojects No. 6492, Pharmaprojects No. 6291, Pharmaprojects No. 6271, Pharmaprojects No. 6267, Pharmaprojects No. 6140, Pharmaprojects No. 6138, Pharmaprojects No. 6083, Pharmaprojects No. 6059, Pharmaprojects No. 6013, Pharmaprojects No. 5330, Pharmaprojects No. 4855, Pharmaprojects No. 4597, Pharmaprojects No. 4368, Pharmaprojects No. 4164, Pharmaprojects No. 3985, Pharmaprojects No. 3495, Pharmaprojects No. 3135, PF-371989, PF-337210, PF-00120130, pelitinib, pegdinetanib, PDGFR-alpha inhibitors, Deciphera, PDGFR inhibitor, Pulmokine, PDGFR inhibitor, Array, PDGF receptor inhibitor, Kyowa, PDGF receptor inhibitor, Array, PDGF kinase inhibitors, Kinex, PD-180970, PD-173956, PD-171026, PD-169540, PD-166285, PD-154233, PD-153035, PD-0166285, PCI-31523, pazopanib hydrochloride (ophthalmic), pan-HER kinase inhib, Ambit-2, pan-HER inhibitor, SUGEN, pan-HER ACL, p56lck inhibitors, BI, OSI-930, OSI-817, OSI-632, OSI-296, ONC-101, ON-88210, ON-045270, NVP-AEW541, NVP-AAK980-NX, NV-50, NSC-242557, NNC-47-0011, NMS-P626, NL-0031, nilotinib, once-daily, nicotinamide derivatives, Bristol-Myers Squibb, neuT MAb, Philadelphia, multi-kinase inhibitors, Amphor, mullerian inhibiting subst, Ma, MS therapy, Critical Outcome Technologies, MP-371, MLN-608, MK-8033, MK-2461, Met/Ron kinase inhibs, SGX, Met/Gab1 antagonist, Semaia, Met RTK antagonists, SUGEN, Met receptor inhibs, Ontogen, Met kinase inhibitor, BMS, Met inhibitors, Amphora, MEDI-548, MED-A300, ME-103, MC-2002, Lyn kinase inhibitor, CRT, Lyn B inhibitors, Onconova, lymphostin, LP-590, leflunomide, SUGEN, lck/Btk kinase inhibitors, AEgera, lck kinase inhibitors, Kinex, lck kinase inhibitors, Celgene, Lck inhibitors, Green Cross, lck inhibitors, Amphora, lck inhibitors, Amgen, lck inhibitors, Abbott, lavendustin A analogues, NIH, LAT inhibitors, NIH, L-000021649, KX-2-377, KST-638, KRX-211, KRX-123, KRN-383, KM-2550, kit inhibitor, Amphora, kinase inhibitors, SGX-2, kinase inhibitors, SGX-1, kinase inhibitors, MethylGene, kinase inhibitors, Amgen, kinase inhibitor, Cephalon, KIN-4104, Ki-8751, Ki-20227, Ki-11502, KF-250706, KDR kinase inhibs, Celltech, KDR kinase inhibitors, Merck & Co-2, KDR kinase inhibitors, Merck & Co-1, Kdr kinase inhibitors, Amgen, KDR inhibitors, Abbott, KDR inhibitor, LGLS, K252a, JNJ-38877605, JNJ-26483327, JNJ-17029259, JNJ-141, Janex-1, JAK3 inhibitors, Pharmacopeia-2, Jak3 inhibitors, Portola, JAK2 inhibitors, Merck & Co, JAK2 inhibitors, Deciphera, JAK2 inhibitors, Amgen, JAK2 inhibitors, Abbott, JAK2 inhibitor, CV, Cytopia, JAK2 inhibitor, cancer, Cytopia, JAK2 inhibitor, Astex, JAK-3 inhibitors, Cellzome, JAK inhibitors, Genentech, JAK inhibitors, BioCryst, JAK inhibitor, Pulmokine, JAK ⅓ inhibitor, Rigel, ITK inhibitors, GlaxoSmithKline, ISU-101, interleukin-2 inducible T-cell kinase inhibitors, Vertex, INSM-18, inherbins, Enkam, IMC-1C11, imatinib, sublingual, Kedem Pharmaceuticals, IGF-1R inhibitor, Allostera, IGF-1 inhibitors, Ontogen, HMPL-010, HM-95091, HM-60781, HM-30XXX series, Her2/neu & EGFR Ab, Fulcrum, HER2 vaccine, ImmunoFrontier, HER-2 binder, Borean, Her-1/Her-2 dual inhibitor, Hanmi, Her inhibitors, Deciphera, HEM-80322, HDAC multi-target inhibitors, Curis, GW-771806, GW-654652, GSK-1838705A, GNE-A, glioblastoma gene therapy, Biogen Idec, genistein, gene therapy, UCSD, focal adhesion kinase inhibitor, Kinex, FMS kinase inhibitors, Cytopia, FLT-3 MAb, ImClone, Flt-3 inhibitor, Elan, Flt ¾ anticancer, Sentinel, FAK/JAK2 inhibitors, Cephalon, FAK inhibitors, Ontogen, FAK inhibitors, Novartis, FAK inhibitors, GlaxoSmithKline, FAK inhibitors, Cytopia, EXEL-6309, Etk/BMX kinase inhibitors, SuperGen, erbstatin, erbB-2 PNV, UAB, erbB-2 inhibitors, Cengent, ER-068224, ephrin-B4 sol receptor, VasGene, ephrin-B4 RTK inhib, VasGene, EphA2 receptor tyrosine kinase inhibitor, Pfizer, ENMD-981693, EHT-102, EHT-0101, EGFR/Her-2 kinase inhibitors, Shionogi, EGFR-CA, EGFR kinase inhibitors, Kinex, EGF-genistein, Wayne, EGF-593A, EG-3306, DX-2240, DP-4577, DP-4157, DP-2629, DP-2514, doramapimod, DNX-5000 series, DN-30 Fab, dianilinophthalimide, deuterated erlotinib, CoNCERT, dendritic cell modulators, Antisoma, DD-2, Jak inhibitors, DD-2, dual Jak3/Syk, DCC-2909, DCC-2157, D-69491, CYT-977, CYT-645, CX-4715, curcumin analogues, Onconova, CUDC-107, CT-100, CT-052923, CS-230, CP-724714, CP-673451, CP-564959, CP-292597, CP-127374, Cmpd-1, CL-387785, CKD-712, CHIR-200131, CH-330331, CGP-53716, CGP-52411, CGI-1746, CGEN-B2, CGEN-241, CFAK-Y15, CEP-37440, CEP-33779, CEP-28122, CEP-2563 dihydrochloride, CEP-18050, CEP-17940, celastrol, CDP-791, CB-173, cancer vaccine, bcr-abl, Mologen, cancer therapeutics, Cephalon, CAB-051, c-Src kinase inhibs, AstraZene, c-Met/Her inhibitors, Decipher, c-Met kinase inhibitor, Cephalon, c-Met inhibitors, Roche, c-Met inhibitor, Merck, c-kit inhibitors, Deciphera, c-kit inhibitors, Cell, c-Abl inhibitors, Plexxikon, c-Abl inhibitors, Onconova, BVB-808, Btk inhibitors, Bristol-Myers Squibb, Btk inhibitor, Pharmacyclics-2, BSF-466895, Brk/PTK6 inhibitors, Merck & Co, BreMel/rGel, BPI-703010, BPI-702001, BP-100-2.01, BMX kinase inhibitors, Amphora, BMS-817378, BMS-754807 back-up, BMS-743816, BMS-577098, BLZ-945, BIW-8556, BIO-106, Behcet's disease therapy, Cr, BAY-85-3474, AZM-475271, AZD-0424, AZ-Tak1, AZ-23, Ax1 kinase inhibitors, SuperGen, Ax1 inhibitors, Deciphera, Ax1 inhibitors, CRT, AVL-101, AV-412, aurora/FLT3 kinase inhibs, Im, AST-6, AST-487, ARRY-872, ARRY-768, ARRY-470, ARRY-333786, apricoxib+EGFR-TKI, Tragara, AP-23994, AP-23485, anticancers, CoNCERT, anticancers, Bracco, anticancers, Avila-4, anticancers, Avila-3, anticancers, Avila-2, anticancer ZFPs, ToolGen, anticancer therapy, Ariad, anticancer MAbs, Xencor-2, anticancer MAbs, Kolltan, antiangiogenic ther, Deciphera, anti-Tie-1 MAb, Dyax, anti-PDGF-B MAbs, Mill, anti-inflammatory, Kinex, anti-inflammatory, Avila, anti-inflammatory ther, Vitae, anti-HER2neu scFv, Micromet, anti-HER2/Flt3 ligand, Symbi, anti-HER2 MAb, Abiogen, anti-Flt-1 MAbs, ImClone, anti-fak oligonucleotides, anti-ErbB-2 MAbs, Enzon, anti-EphA4 MAb, MedImmune, anti-EGFRvIII MAbs, Amgen, anti-EGFR MAb, Xencor, anti-EGFR immunotoxin, IVAX, anti-CD20/Flt3 ligand, Symbi, Anti-Cancer Ligands, Enchira, anti-ALK MAb, MedImmune, angiopoietins, Regeneron, AMG-Jak2-01, AMG-458, AMG-191, ALK inhibitors, PharmaDesign, ALK inhibitors, Lilly, ALK inhibitors, Cephalon-2, AI-1008, AHNP, Fulcrum, AGN-211745, AGN-199659, AG-957, AG-1295, AEE-788, and ADL-681.

ErbB tyrosine kinase inhibitor (ERbB) include but are not limited to; vandetanib, lapatinib ditosylate, gefitinib, erlotinib, afatinib, XL-647, neratinib, nelipepimut-S, dovitinib lactate, dacomitinib, varlitinib, RAF-265, PR-610, pozitinib, KD-020, BMS-690514, AZD-8931, AVX-901, AVL-301, AE-37, AC-480, VM-206, theliatinib, IDN-6439, HM-61713, epitinib, CUDC-101, cipatinib, Z-650, SN-34003, SN-29966, MT-062, CST-102, ARRY-380, XL-999, vatalanib, TAK-285, SU-5271, PKI-166, Pharmaprojects No. 4960, Pharmaprojects No. 3624, mubritinib, KSB-102, GW-282974, EMD-55900, CNF-201 series, canertinib dihydrochloride, cancer vaccine, Ajinomoto, breast cancer therapy, Galapago, BIBX-1382, AZD-4769, Argos, AP-23464, anti-HER2/neu mimetic, Cyclacel, anti-HER-2/neu antisense, Tekm, AG-18, ZM-254530, ZD-1838, VEGFR/EGFR inhib, Amphora, VEGF-TK inhibitors, AstraZeneca, V-930, RNAi cancer therapy, Benitec Biopharma, RM-6427, RB-200h, PX-104.1, Pharmaprojects No. 6291, Pharmaprojects No. 6271, Pharmaprojects No. 4164, Pharmaprojects No. 3985, Pharmaprojects No. 3495, pelitinib, PD-169540, PD-166285, PD-154233, PD-153035, pan-HER kinase inhib, Ambit-2, pan-HER inhibitor, SUGEN, pan-HER ACL, ON-045270, NSC-242557, NL-0031, mullerian inhibiting subst, Ma, ME-103, kinase inhibitors, Amgen, JNJ-26483327, ISU-101, INSM-18, inherbins, Enkam, HM-60781, HM-30XXX series, Her2/neu & EGFR Ab, Fulcrum, HER2 vaccine, ImmunoFrontier, HER-2 binder, Borean, Her-1/Her-2 dual inhibitor, Hanmi, Her inhibitors, Deciphera, HEM-80322, gene therapy, UCSD, erbB-2 PNV, UAB, erbB-2 inhibitors, Cengent, EHT-102, EGFR/Her-2 kinase inhibitors, Shionogi, EGFR-CA, EGFR kinase inhibitors, Kinex, EGF-593A, dianilinophthalimide, deuterated erlotinib, CoNCERT, D-69491, curcumin analogues, Onconova, CUDC-107, CP-724714, CP-292597, CL-387785, CGEN-B2, CAB-051, c-Met/Her inhibitors, Decipher, BreMel/rGel, BIO-106, AV-412, AST-6, ARRY-333786, apricoxib+EGFR-TKI, Tragara, anticancers, CoNCERT, anticancer MAbs, Xencor-2, anti-HER2neu scFv, Micromet, anti-HER2 MAb, Abiogen, anti-ErbB-2 MAbs, Enzon, anti-EGFRvIII MAbs, Amgen, anti-EGFR MAb, Xencor, anti-EGFR immunotoxin, IVAX, Anti-Cancer Ligands, Enchira, AHNP, Fulcrum, AEE-788, and ADL-681.

MEK1 or MEK2 (MEK) include, but are not limited to: Trametinib, ARRY-438162, WX-554, Selumetinib, Pimasertib, E-6201, BAY-86-9766, TAK-733, PD-0325901, GDC-0623, BI-847325, AS-703988, ARRY-704, Antroquinonol, CI-1040, SMK-17, RO-5068760, PD-98059, and ER-803064.

PIK3CA related treatments include, but are not limited to: perifosine, BKM-120, ZSTK-474, XL-765, XL-147, PX-866, PKI-587, pictilisib, PF-04691502, BYL-719, BEZ-235, BAY-80-6946, PWT-33597, PI3 kinase/mTOR inhibitor, Lilly, INK-1117, GSK-2126458, GDC-0084, GDC-0032, DS-7423, CUDC-907, BAY-1082439, WX-037, SB-2343, PI3/mTOR kinase inhibitors, Amgen, mTOR inhibitor/PI3 kinase inhibitor, Lilly-1, LOR-220, HMPL-518, HM-032, GNE-317, CUDC908, CLR-1401, anticancers, Progenics, anticancer therapy, Sphaera Pharma-1, AMG-511, AEZS-136, AEZS-132, AEZS-131, AEZS-129, pictilisib, companion diagnostic, GDC-0980, companion diagnostic, GDC-0032, companion diagnostic, AZD-8055, VEL-015, SF-2523, SF-2506, SF-1126, PX-2000, PKI-179, PI3K p110alpha inhibitors, Ast, PI3K inhibitors, Semafore-2, PI3K inhibitors, Invitrogen, PI3K inhibitor conjugate, Semaf, PI3K conjugates, Semafore, PI3-irreversible alpha inhibitors, Pathway, PI3-alpha/delta inhibitors, Pathway Therapeutics, PI3-alpha inhibitors, Pathway Therapeutics, PI3 kinase inhibitors, Wyeth, PI3 kinase inhibitors, Telik, PI3 kinase alpha selective inhibitors, Xcovery, PI-620, PF-4989216, PF-04979064, PF-00271897, PDK1 inhibitors, GlaxoSmithKline, ONC-201, KN-309, isoform-selective PI3a/β kinase inhibitors, Sanofi, inositol kinase inhibs, ICRT, HM-5016699, hepatocellular carcinoma therapy, Sonitu, GSK-1059615, glioblastoma therapy, Hoffmann-La Roche, EZN-4150, CU-906, CU-903, CNX-1351, anti-thrombotic, Cerylid, 4-methylpteridinones.

Treatments directed to ALK include, but are not limited to: crizotinib, companion diagnostic, AbbVie, crizotinib, TSR-011, RG-7853, LDK-378, AP-26113, X-396, ASP-3026, NMS-E628, DLX-521, aurora kinase+ALK inhibitor, Sareum, aurora kinase+ALK inhibitor, AstraZeneca, ALK inhibitors, AstraZeneca, Alk inhibitor, Cephalon-3, ALK inhibitor, Aurigene Discovery Technologies, LDK-378, companion diagnostic, crizotinib, companion diagnostic, Roche, TAE-684, kinase inhibitor, Cephalon, GSK-1838705A, EXEL-6309, Cmpd-1, CEP-37440, CEP-28122, CEP-18050, cancer therapeutics, Cephalon, anti-ALK MAb, MedImmune, ALK inhibitors, PharmaDesign, ALK inhibitors, Lilly, ALK inhibitors, and Cephalon-2.

Treatments directed to RET include, but are not limited to: vandetanib, sunitinib malate, sorafenib, regorafenib, cabozantinib, SAR-302503, motesanib diphosphate, apatinib, RET kinase inhibitor, Bionomics, NMS-173, MG-516, sorafenib bead, Biocompatibles, RET inhibitors, Cell T, MP-371, kinase inhibitors, MethylGene, JNJ-26483327, DCC-2157, and AST-487.

Accordingly, these and other agents can be used alone or in combination to treat NSCLC and can be included as an actionable treatment recommendation as disclosed herein.

Kits

In another aspect, the present invention provides kits for practicing the assays described herein using nucleic acids specific for the polynucleotides relating to the CDKN2A gene, CDKN2A gene or both.

Kits for carrying out the method of the invention typically include a probe that comprises a nucleic acid sequence that specifically binds to polynucleotides relating to the CDKN2A gene, CDKN2A gene or both, and a label for detecting the presence of the probe.

In some embodiments, the kits comprise reagents to amplify the CDKN2A gene comprising a loss of function mutation, or portion of the gene comprising the loss of function mutation. In some embodiments, the reagents are PCR primer sets.

In some embodiments, the kits comprise reagents to reverse transcribe a RNA transcript encoded by the CDKN2A gene comprising a loss of function mutation. In some embodiments, the reagents are RT-PCR sets.

It is understood that the embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

Example 1—Identification of Biomarkers

Cyclin-dependent kinase inhibitor 2A, (CDKN2A, p16Ink4A) also known as multiple tumor suppressor 1 (MTS-1), is a tumor suppressor protein, that in humans is encoded by the CDKN2A gene. P16 plays an important role in regulating the cell.

G1/S-specific cyclin-D1 is a protein that in humans is encoded by the CCND1 gene. The protein encoded by this gene belongs to the highly conserved cyclin family, whose members are characterized by a dramatic periodicity in protein abundance throughout the cell cycle. Cyclins function as regulators of CDKs (Cyclin-dependent kinase). Different cyclins exhibit distinct expression and degradation patterns which contribute to the temporal coordination of each mitotic event. This cyclin forms a complex with and functions as a regulatory subunit of CDK4 or CDK6, whose activity is required for cell cycle G1/S transition. This protein has been shown to interact with tumor suppressor protein Rb and the expression of this gene is regulated positively by Rb. Mutations, amplification and overexpression of this gene, which alters cell cycle progression, are observed frequently in a variety of tumors and may contribute to tumorigenesis.

In order to identify squamous cell carcinoma biomarkers that could be used to predict clinical outcome for a human subject diagnosed with the cancer, The Cancer Genome Atlas was examined for patient data relating to lung squamous cell carcinoma. The patient information was then used to establish a correlation between various markers identified and clinical outcome for the patients diagnosed to have stages 1-4 cancer.

Gene expression, mutation, and copy number changes of CDKN2A and CCND1 genes were characterized in a cohort of squamous cell lung carcinoma patients from The Cancer Genome Atlas and associations with clinical endpoints were identified. Genetic aberrations were identified that associated with poor outcome of patients with early stage squamous cell lung carcinoma (SCLC), These two events, cyclin-dependent kinase inhibitor 2A (CDKN2A gene mutation (i.e., mutation of the gene sequence or gene deletion) and cyclin D1 (CCND1) gene amplification (i.e., increase in copy number) each control the activity of G1/S cell division cycle kinases CDK4/6. Thus, the activation of the G1/S pathway is prognostic for poor outcome in early stage squamous cell lung carcinoma.

FIG. 1 shows the analysis of mixed-stage patient population of 175 patients with squamous cell lung carcinoma. In this figure and the following figures, the upper curve shows the events associated with each patient who did not have an aberration of the G1/S pathway, while the lower curves shows the events associated with each patient who had an aberration of the G1/S pathway. In each curve, "x" indicates death, while "o" represents survival at last follow-up. The data show that the G1/S pathway aberration is associated with poor outcome for SCLC.

Figure 2A:
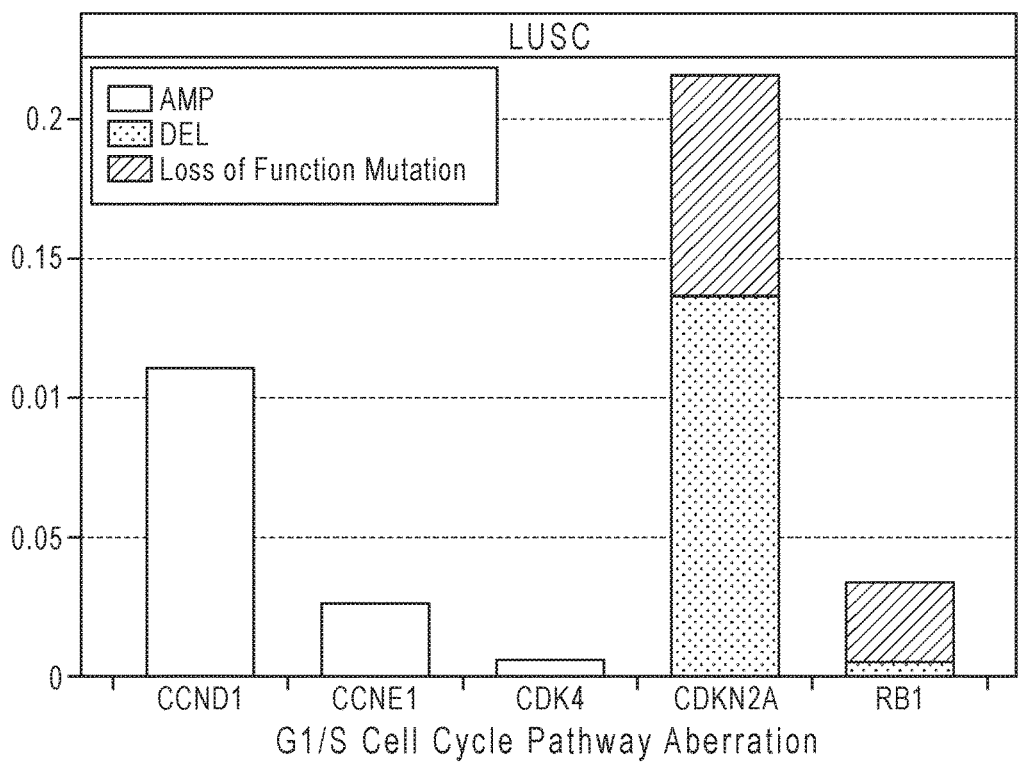
FIG. 2A is a graph that shows that the G1/S pathway aberration is dominated by CDKN2A gene loss and CCND1 gene amplification.
Figure 2B:
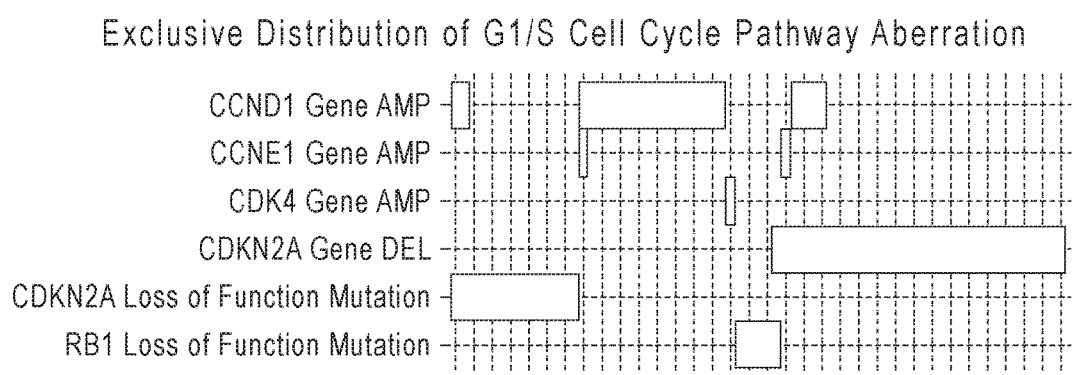
FIG. 2B is a chart that shows that the G1/S pathway aberration is dominated by CDKN2A gene loss and CCND1 gene amplification.

FIGS. 2A and 2B show that the G1/S pathway aberration is dominated by CDKN2A gene loss and CCND1 gene amplification.

Figure 3A:
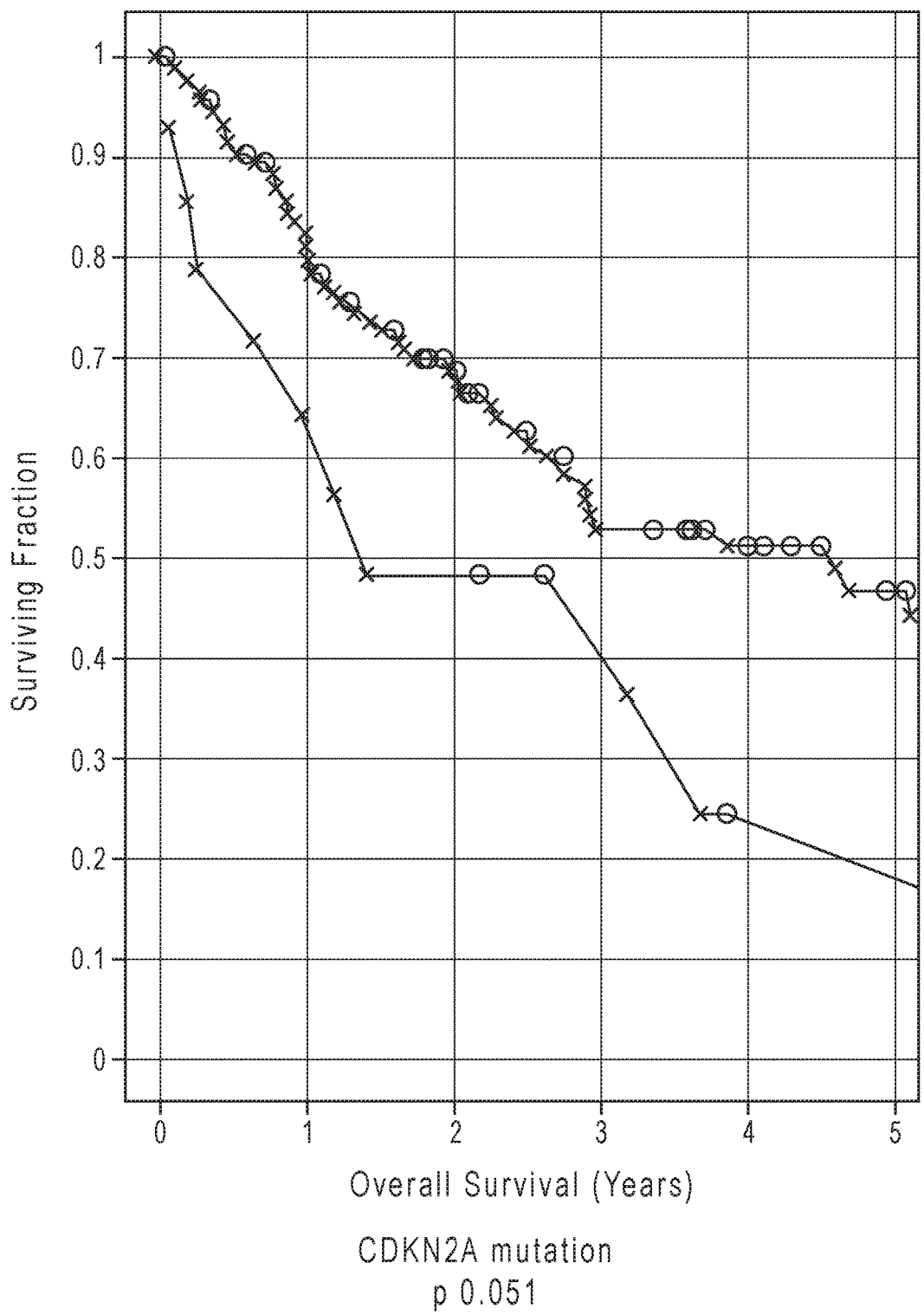
FIG. 3A is a graph that shows that the poor outcome of patients of a mixed-stage population with respect to the individual G1/S cell cycle pathway aberration and CDKN2A gene mutation.
Figure 3B:
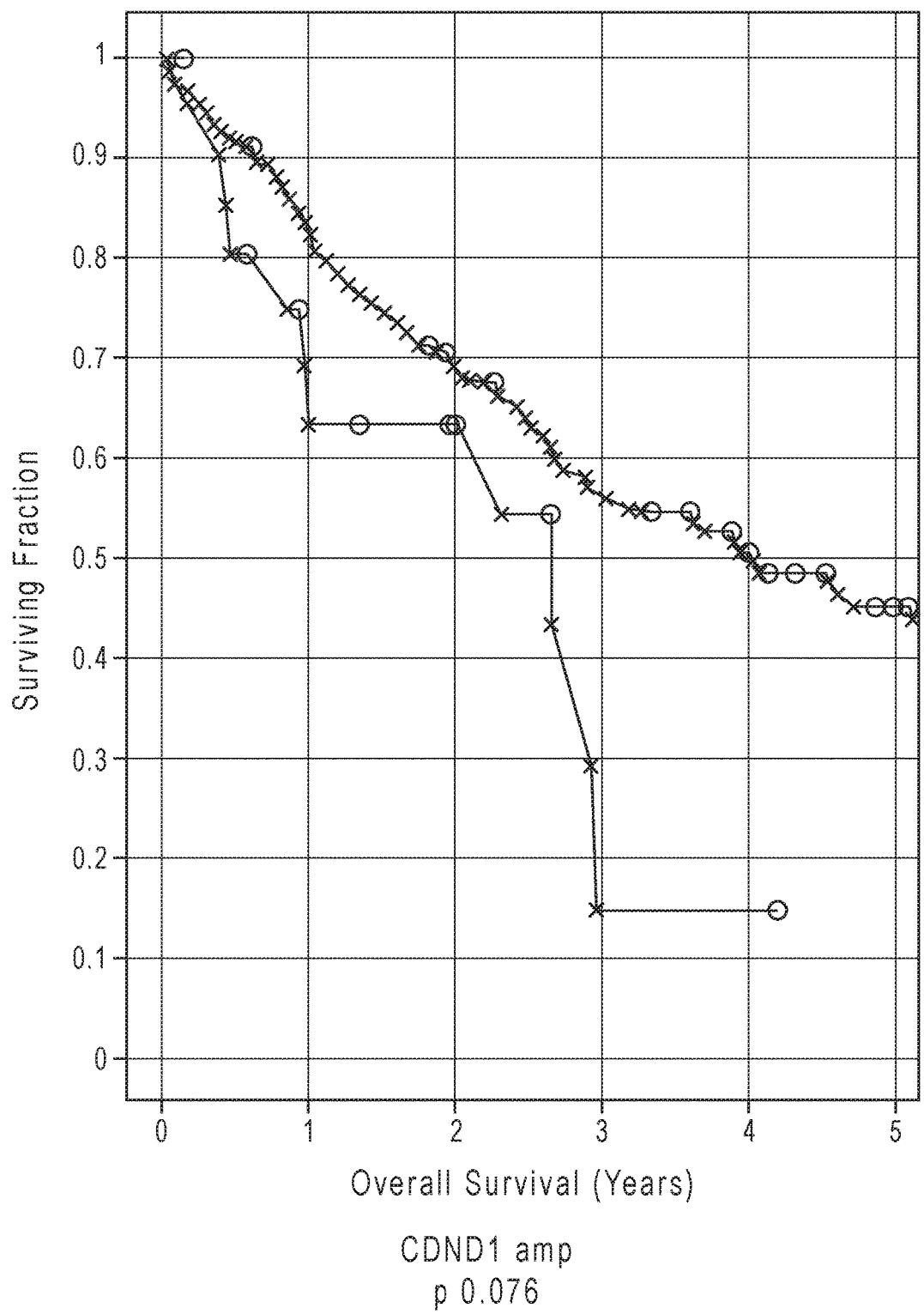
FIG. 3B is a graph that shows that the poor outcome of patients of a mixed-stage population with respect to the individual G1/S cell cycle pathway aberration and CCND1 gene amplification.
Figure 3C:
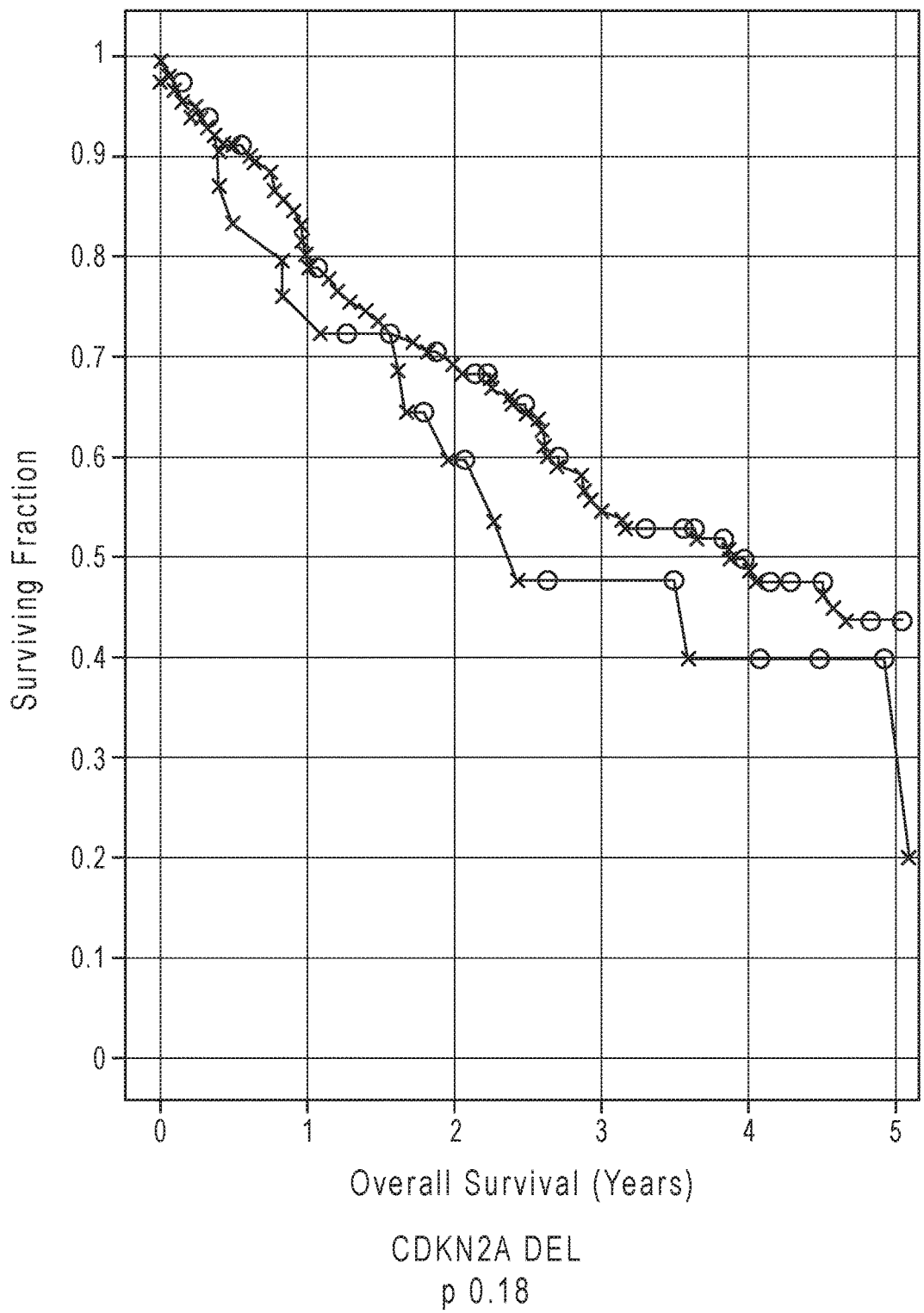
FIG. 3C is a graph that shows that the poor outcome of patients of a mixed-stage population with respect to the individual G1/S cell cycle pathway aberration and CDKN2A gene deletion.
Figure 4A:
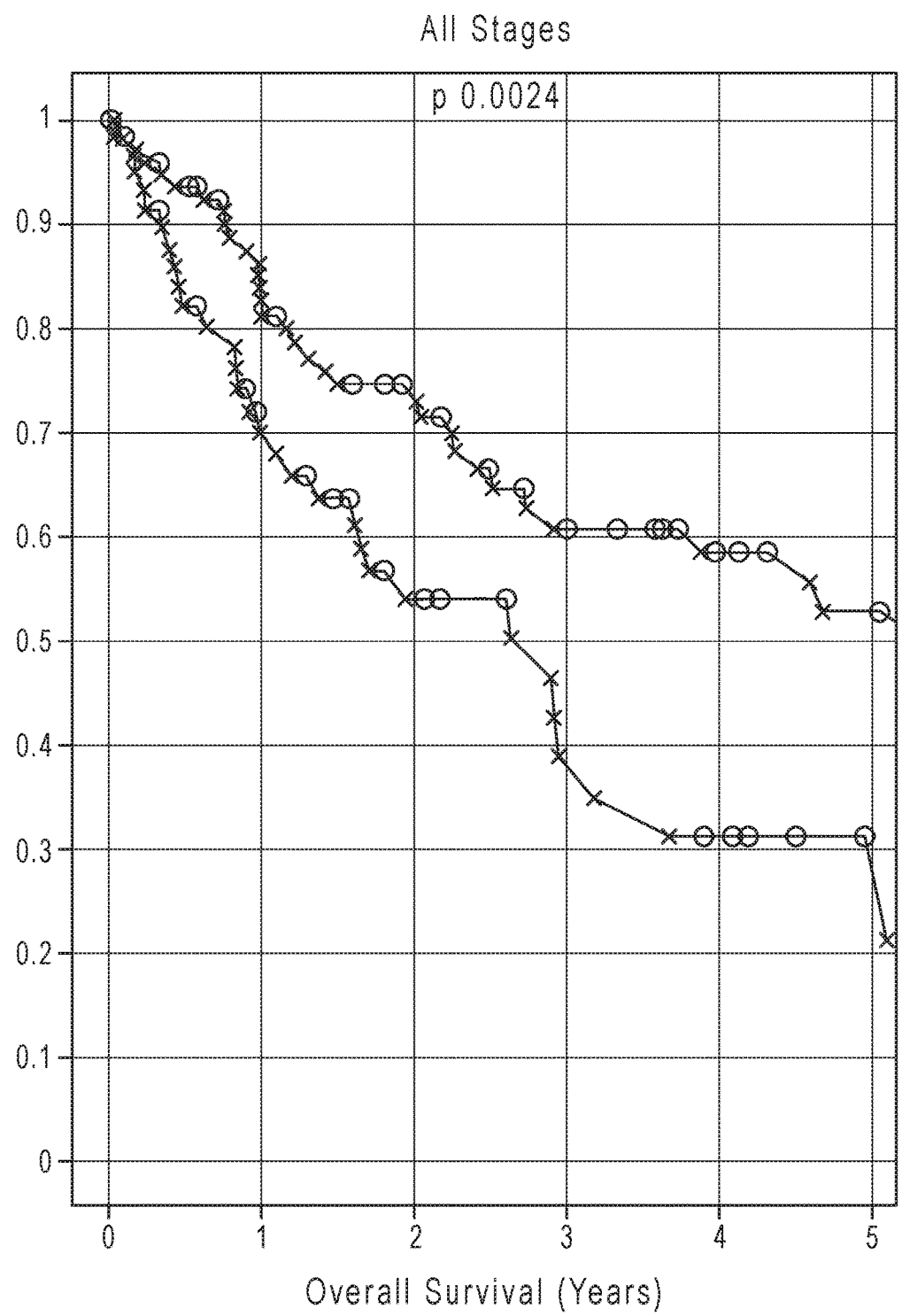
FIG. 4A shows a comparison of the association of the G1/S pathway aberration with poor outcome for all stages of SCLC.
Figure 4B:
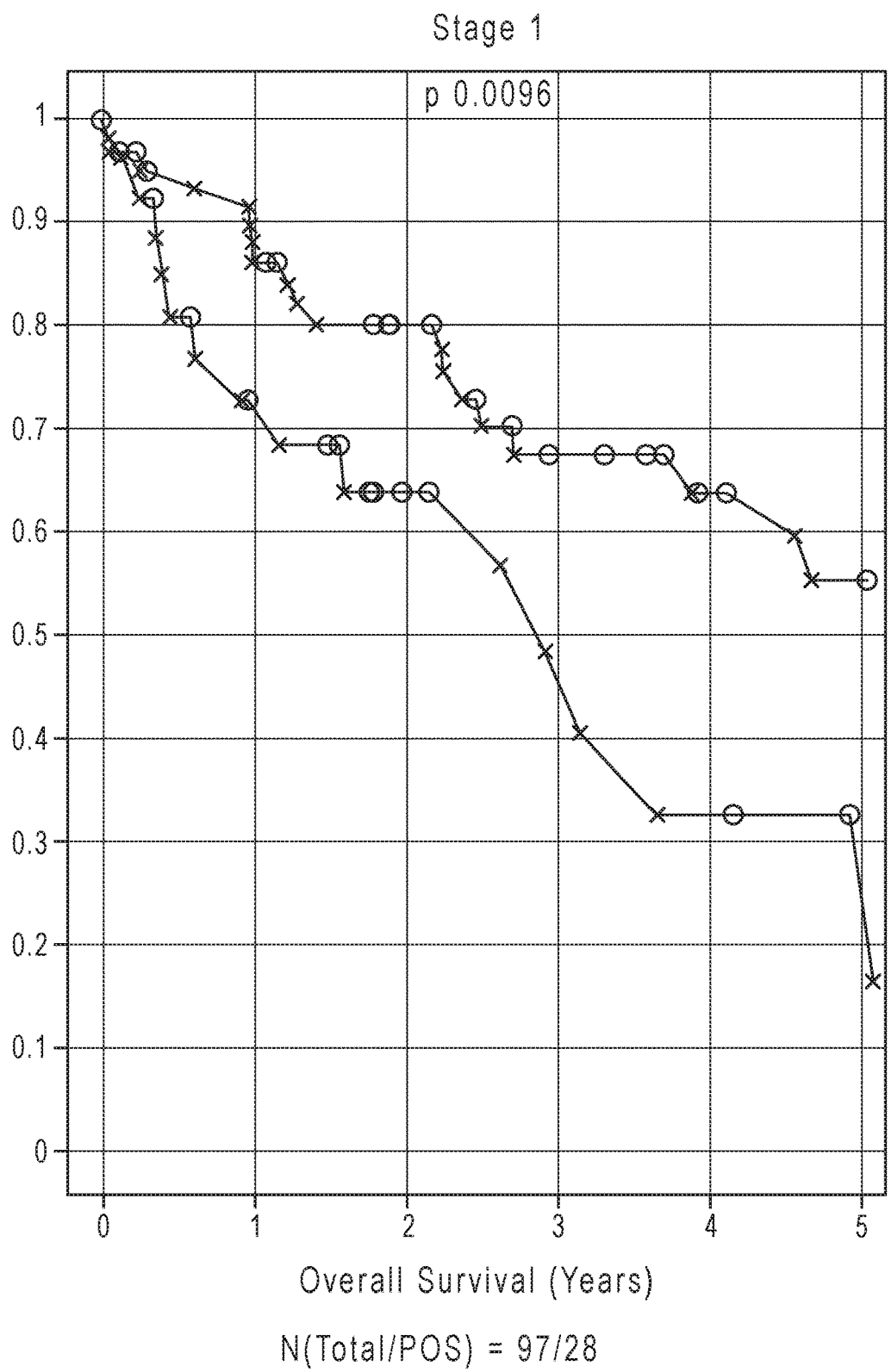
FIG. 4B shows a comparison of the association of the G1/S pathway aberration with poor outcome for stage 1 of SCLC.
Figure 4C:
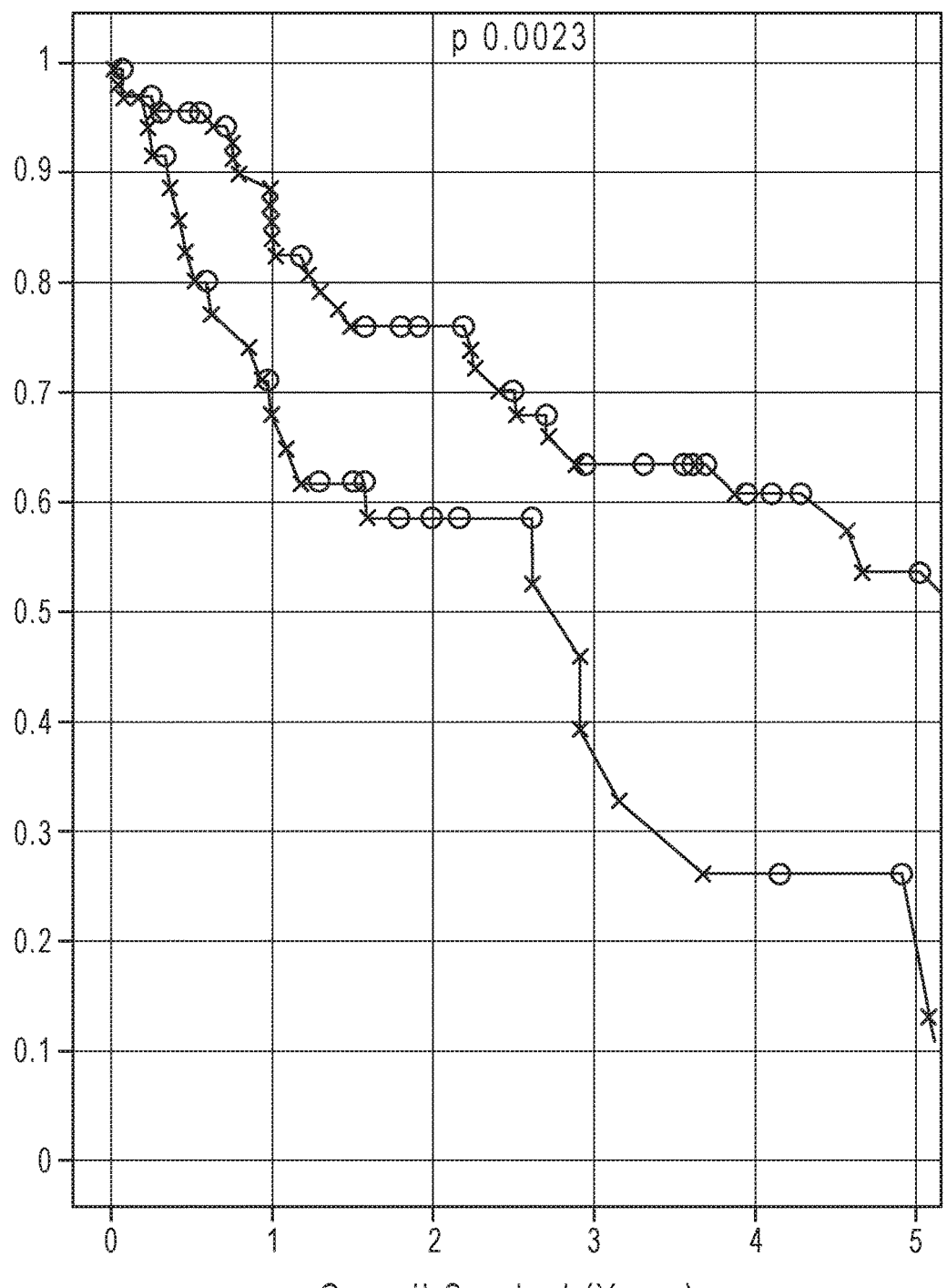
FIG. 4C shows a comparison of the association of the G1/S pathway aberration with poor outcome for stages 1 and 2 of SCLC.
Figure 4D:
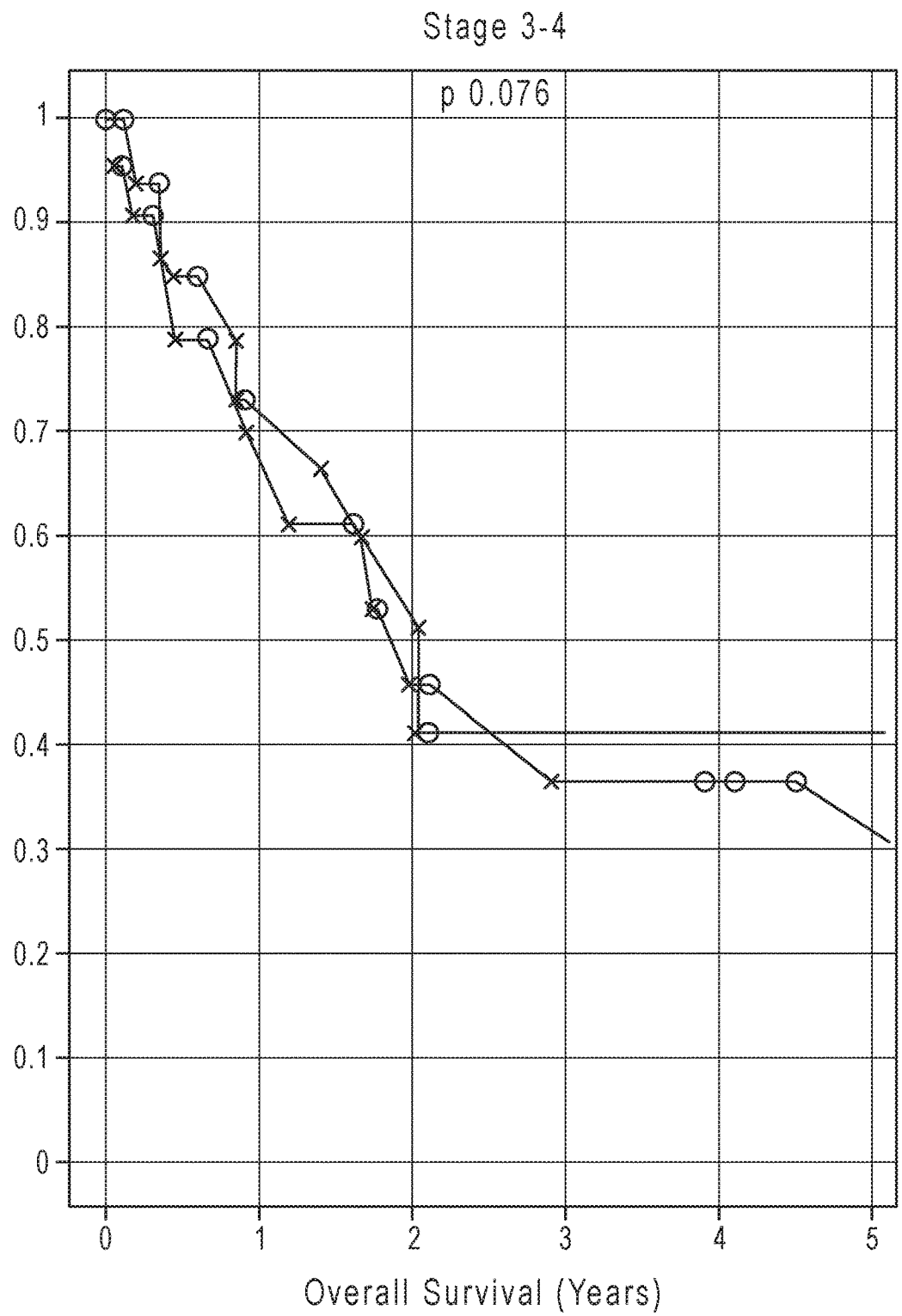
FIG. 4D shows a comparison of the association of the G1/S pathway aberration with poor outcome for stages 3 and 4 of SCLC.

FIG. 3 shows that the poor outcome of patients of a mixed-stage population with respect to the individual G1/S cell cycle pathway aberrations, CDKN2A gene mutation, CCND1 gene amplification, and CDKN2A gene deletion. The data show that these biomarkers have utility as prognostic of poor outcome for SCLC.

FIG. 4 shows a comparison of the association of the G1/S pathway aberration with poor outcome for all stages, stage 1, stages 1 and 2, and stages 3 and 4 of SCLC. The association with poor outcome is observed specifically in early-stage SCLC.

Figure 5A:
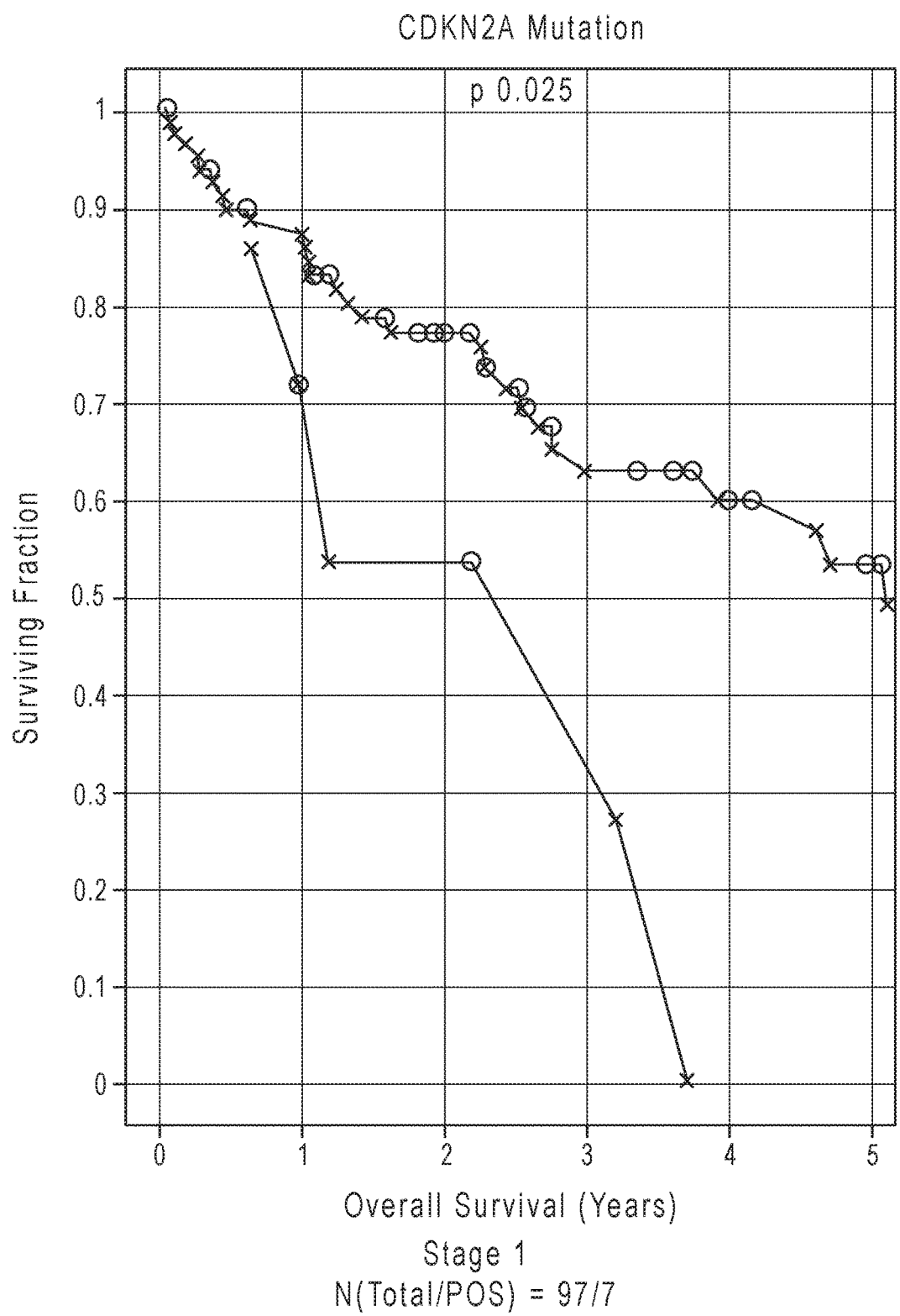
FIG. 5A shows association of poor outcome of early-stage SCLC with respect to G1/S pathway aberration and CDKN2A mutation.
Figure 5B:
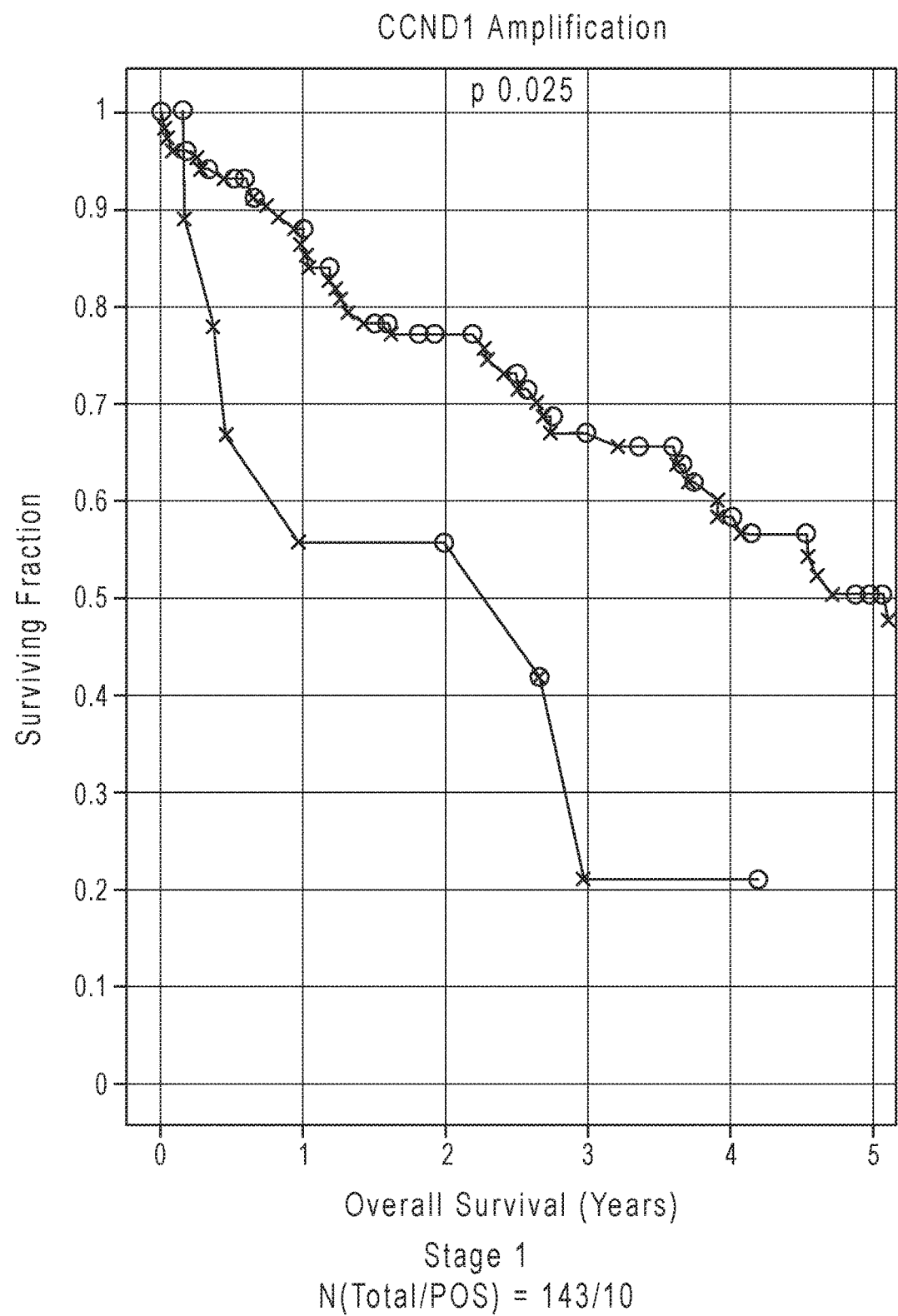
FIG. 5B shows association of poor outcome of early stage SCLC with respect to G1/S pathway aberration and CCND1 amplification.

FIG. 5 shows association of poor outcome of early-stage SCLC with respect to G1/S pathway aberration, CDKN2A mutation and CCND1 amplification.

Figure 6A:
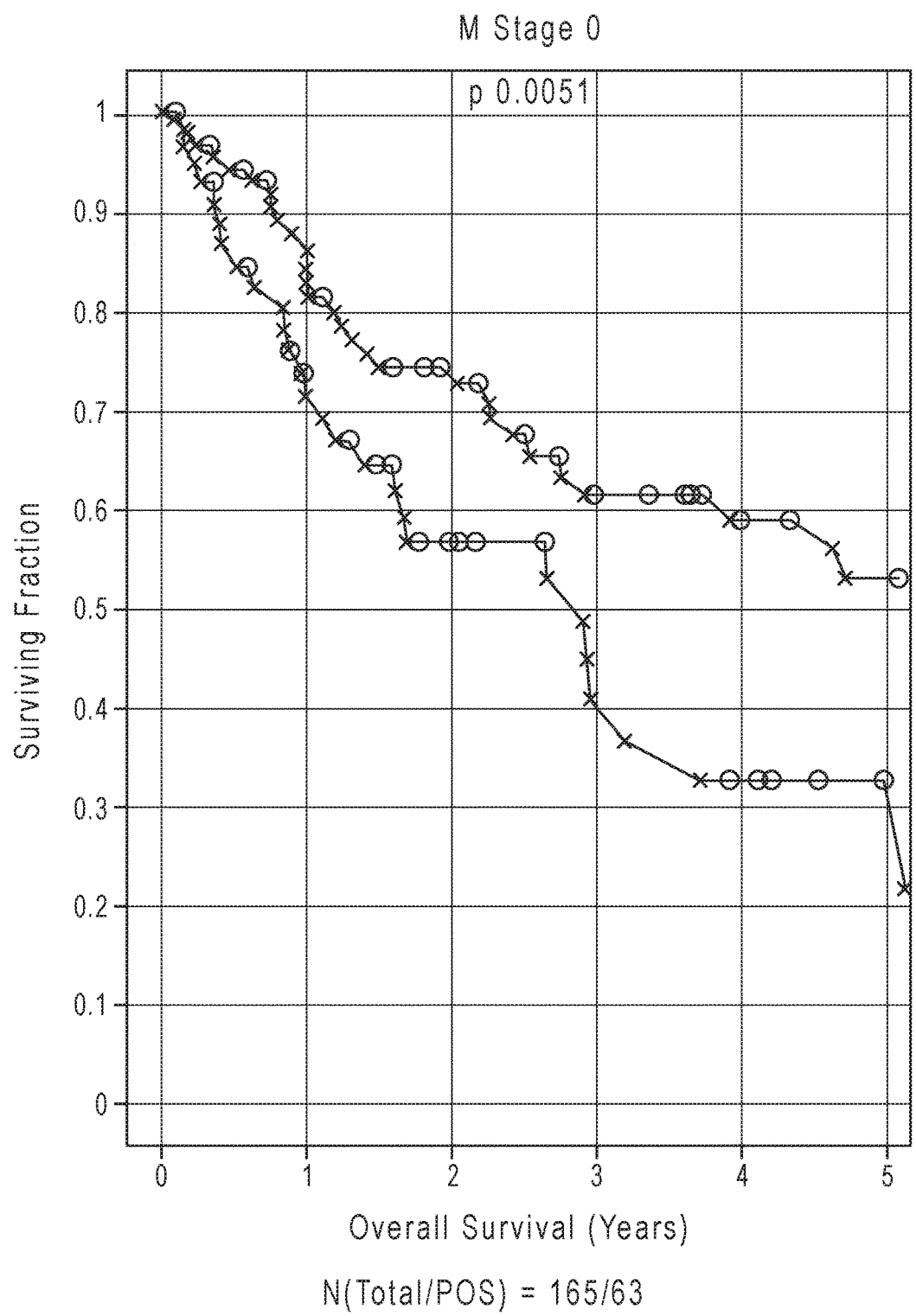
FIG. 6A shows that the association of the G1/S pathway aberration with poor outcome is observed in early stage SCLC as measured by M Stage 0.—Primary Tumor (T), Regional Lymph Nodes (N), Distant Metastasis (M) stages 1 to 2.
Figure 6B:
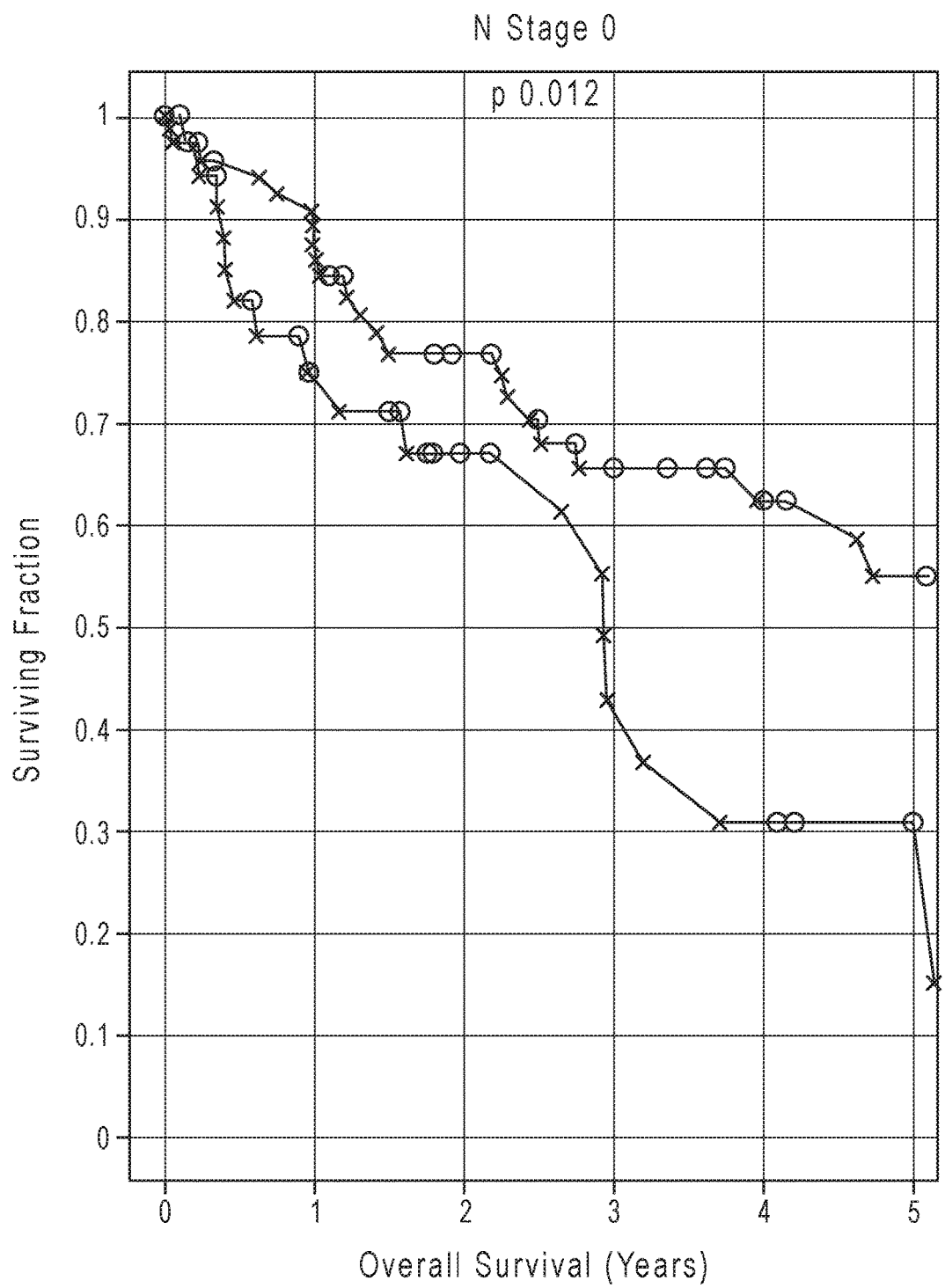
FIG. 6B shows that the association of the G1/S pathway aberration with poor outcome is observed in early stage SCLC as measured by N Stage 0. Primary Tumor (T), Regional Lymph Nodes (N), Distant Metastasis (M) stages 1 to 2.
Figure 6C:
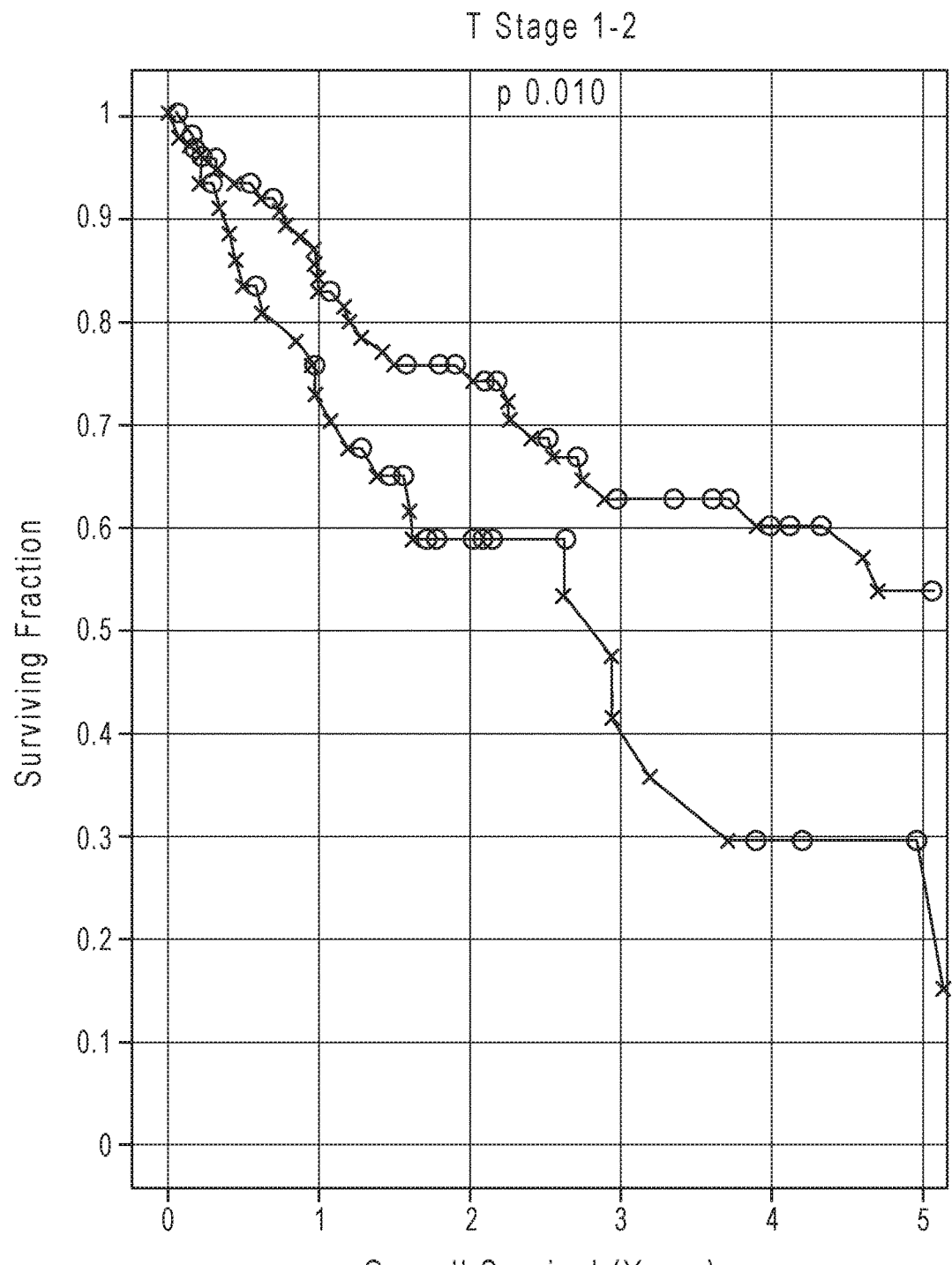
FIG. 6C shows that the association of the G1/S pathway aberration with poor outcome is observed in early stage SCLC as measured by T Stage 1-2. Primary Tumor (T), Regional Lymph Nodes (N), Distant Metastasis (M) stages 1 to 2.

FIG. 6 shows that the association of the G1/S pathway aberration with poor outcome is observed in early stage SCLC as measured by other staging definitions—Primary Tumor (T), Regional Lymph Nodes (N), Distant Metastasis (M) stages 1 to 2.

Thus, the biomarkers CDKN2A gene mutation and CCND1 gene amplification, are associated with poor outcome for early stage SCLC.

Example 2—Method of Predicting Clinical Outcome

A sample of the cancer tumor from a subject diagnosed as having squamous cell lung cancer is examined by PCR and next generation sequencing for the presence of a loss of function mutation in the CDKN2A gene or deletion of this gene. In addition, the sample is examined by copy number variation methodologies for the presence of an increase in the copy number of the CCND1 gene. Where the sample is determined to have a loss of function mutation in the CDKN2A gene or deletion of this gene, and an increase in the copy number of the CCND1, a prediction is made that the subject has an increased likelihood of a negative clinical outcome. Where the sample is determined to have an absence of a loss of function mutation in the CDKN2A gene or deletion of this gene or an absence of an increase in the copy number of the CCND1 gene, a prediction is made that the subject has an increased likelihood of a positive clinical outcome.

Example 3—Method for Determining Treatment Plan

In order to determine a treatment plan for a human subject having squamous cell lung cancer, a sample of the subject's cancer tumor is examined by PCR and next generation sequencing for the presence of a loss of function mutation in the CDKN2A gene or deletion of this gene. In addition, the sample is also examined by copy number variation methodologies for the presence of an increase in the copy number of the CCND1 gene. Where the sample is determined to have a loss of function mutation in the CDKN2A gene or deletion of this gene, and an increase in the copy number of the CCND1, a prediction is made that the subject has an increased likelihood of a negative clinical outcome. Where the sample is determined to have an absence of a loss of function mutation in the CDKN2A gene or deletion of this gene or an absence of an increase in the copy number of the CCND1 gene, a prediction is made that the subject has an increased likelihood of a positive clinical outcome. The prediction is then used to determine a risk assessment for a 5-year mortality. Based on this risk assessment, an appropriate treatment plan is devised for the patient.

Example 4—System for Determining Treatment Plan for Human Subject

A human subject having squamous cell lung cancer undergoes surgery to remove the lung tumor. A sample of the tumor is sent to a test laboratory to be examined for the presence of a loss of function mutation in the CDKN2A gene or deletion of this gene. In addition, the sample is also examined for the presence of an increase in the copy number of the CCND1 gene. The test results are then put into a patient database which resides on a processor at this laboratory. The data entered into this database are the test results determining if there is a loss of function mutation in the CDKN2A gene or deletion of the gene in this sample and if there is an increase in the copy number of the CCND1 gene in the sample.

The test results are then electronically transmitted from this processor to another processor at another location. The processor at the second site will contain a treatment protocol database that is populated with one or more treatment protocols that provide guidelines for treating squamous cell lung cancer patients and containing a correlation of the presence of a loss of function mutation in the CDKN2A gene or deletion of the gene with an increase in the copy number of the CCND1 gene, which correlation is that these test results are indicative of increased likelihood of a negative clinical outcome. Based on the test results, the processor determines a treatment protocol for this subject.

Example 5—Identifying a Subject as Candidate for Post-Surgical Adjuvant Therapy

A human subject having squamous cell lung cancer undergoes surgery to remove the lung tumor. A sample of the tumor is sent to a test laboratory to be examined for the presence of a loss of function mutation in the CDKN2A gene or deletion of this gene. In addition, the sample is examined for the presence of an increase in the copy number of the CCND1 gene. Where the presence of a loss of function mutation in the CDKN2A gene or deletion of this gene and the presence of an increase in the copy number of the CCND1 gene is determined, the determination is made that these results correlates with increased likelihood of a negative clinical outcome. Based on this, the patient is identified as a candidate for post-surgical adjuvant therapy.

Example 6—Method of Treating Squamous Cell Lung Cancer

A human patient having squamous cell lung cancer undergoes surgery to remove the lung tumor. A sample of the tumor is sent to a test laboratory to be examined for the presence of a loss of function mutation in the CDKN2A gene or deletion of this gene. In addition, the sample is examined for the presence of an increase in the copy number of the CCND1 gene. Where the presence of a loss of function mutation in the CDKN2A gene or deletion of this gene and the presence of an increase in the copy number of the CCND1 gene is determined, the patient is identified as having squamous cell lung cancer cells which contain a loss of function mutation in the CDKN2A gene or deletion of the gene and increase in the copy number of the CCND1 gene. Based on this identification, the patient is treated with a post-surgical adjuvant therapy.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of providing a clinical outcome predictor for a human subject diagnosed with early stage squamous cell lung carcinoma comprising:
   a) obtaining a biological sample comprising early stage squamous cell lung carcinoma cancer cells from a human subject diagnosed with early stage squamous cell lung carcinoma;
   b) detecting whether a loss of function mutation or a deletion of the cyclin-dependent kinase inhibitor 2A (CDKN2A) gene is present in the subject by determining the presence or absence of a loss of function mutation or a deletion in the CDKN2A gene by next generation sequence examination in the biological sample comprising cancer cells; and
   c) detecting whether an increase in the copy number of the G1/S-specific cyclin-D1 (CCND1) gene is present in the subject by determining the presence or absence of an increase in the copy number of the CCND1 gene by comparative genomic hybridization examination in the biological sample comprising cancer cells; and
   d) combining the detecting result of b) and c) and providing a clinical outcome predictor for the subject,
   wherein the presence of a loss of function mutation or deletion in the CDKN2A gene and/or the presence of an increase in the copy number of the CCND1 gene is a predictor of a negative clinical outcome, and wherein the absence of a loss of function mutation or deletion in the CDKN2A gene and the absence of an increase in the copy number of the CCND1 gene is a predictor of a positive clinical outcome.

2. The method of claim 1, wherein the loss of function mutation in the CDKN2A gene is a missense mutation, nonsense mutation, or frameshift mutation, or any combination thereof.

3. The method of claim 2, wherein the missense mutation is any of D108G, D108N, D108Y, G125R, P114L mutation, or any combination thereof.

4. The method of claim 1, wherein the increase in the copy number of the CCDN1 gene is greater than or equal to 4.

5. The method of claim 1, wherein the next generation sequence examination of a loss of function mutation or deletion in the CDKN2A gene comprises contacting the biological sample with reagents and
   a) amplifying the CDKN2A gene or a portion thereof thereby providing an amplification product of the gene or portion thereof, or
   b) reverse transcribing a RNA transcript encoded by the CDKN2A gene and amplifying the reverse transcription product thereby providing an amplification product of the gene or portion thereof.

6. The method of claim 5, wherein the next generation sequencing examination comprises sequencing the entire coding region of the CDKN2A gene.

7. The method of claim 5, wherein the next generation sequencing examination comprises qPCR.

8. The method of claim 5, wherein the reagents are oligonucleotides.

9. The method of claim 5, wherein the reagents are PCR primer sets.

10. The method of claim 5, wherein the reagents are RT-PCR primer sets.

11. The method of claim 1, wherein the squamous cell lung carcinoma is stage I.

12. The method of claim 1, wherein the squamous cell lung carcinoma is stage II.

13. The method of claim 1, wherein the biological sample is obtained from a surgically resected tumor.

14. The method of claim 1, wherein the biological sample is obtained from lymph node or a distant metastasis sample.

15. The method of claim 1, wherein the biological sample is obtained from a blood sample.

16. A method of identifying a negative clinical outcome predictor consisting of a loss of function mutation or deletion in the cyclin-dependent kinase inhibitor 2A (CDKN2A) gene and an increased copy number of the G1/S-specific cyclin-D1 (CCND1) gene in a biological sample of a human subject diagnosed with early stage squamous cell lung carcinoma, the method comprising:
   a) obtaining a biological sample comprising early stage squamous cell lung carcinoma cancer cells from a human subject diagnosed with early stage squamous cell lung carcinoma;
   b) detecting the presence of a loss of function mutation or a deletion in the CDKN2A gene by next generation sequence examination in the biological sample comprising cancer cells; and
   c) detecting whether an increase in the copy number of the CCND1 gene is present in the subject by determining the presence or absence of an increase in the copy number of the CCND1 gene by comparative genomic hybridization examination in the biological sample comprising cancer cells;
   wherein detecting the presence of a loss of function mutation or deletion in the CDKN2A gene and the presence of an increase in the copy number of the CCND1 gene identifies the negative clinical outcome predictor.

17. The method of claim 16, wherein the biological sample is obtained from a surgically resected tumor.

18. The method of claim 16, wherein the biological sample is obtained from lymph node, a distant metastasis sample, or a blood sample.

19. A method of treating early stage squamous cell lung carcinoma in a patient comprising;
   a) obtaining a biological sample from a patient containing early stage squamous cell lung carcinoma cells obtained from surgical resection of a tumor;
   b) detecting the presence of a loss of function mutation or a deletion of the cyclin-dependent kinase inhibitor 2A (CDKN2A) gene in the subject by determining the presence of a loss of function mutation or a deletion in the CDKN2A gene in the biological sample by next generation sequence examination; and
   c) detecting whether an increase in the copy number of the G1/S-specific cyclin-D1 (CCND1) gene is present in the subject by determining the presence or absence of an increase in the copy number of the CCND1 gene in the biological sample by comparative genomic hybridization examination; and d) treating the patient having early stage squamous cell lung carcinoma cells comprising a loss of function mutation or a deletion in the CDKN2A gene and an increase in the copy number of the CCDN1 gene with post-surgical adjuvant therapy.

20. The method of claim 19, wherein the post-surgical adjuvant therapy is chemotherapy, radiation therapy, or a combination thereof.

* * * * *